US00RE42507E

(19) United States
(12) Reissued Patent
Wilkinson et al.

(10) Patent Number: US RE42,507 E
(45) Date of Reissued Patent: Jun. 28, 2011

(54) SURGICAL SCALPEL

(75) Inventors: Bradley M. Wilkinson, North Haledon, NJ (US); Anthony J. Kosinski, New Providence, NJ (US); Charles Hwang, Waltham, MA (US); Ann Eckert, Nazareth, PA (US); Simon Cohn, Rutherford, NJ (US); Noel Gharibian, Glendale, CA (US)

(73) Assignee: Aspen Surgical Products, Inc., Caledonia, MI (US)

( * ) Notice: This patent is subject to a terminal disclaimer.

(21) Appl. No.: 09/771,394

(22) Filed: Jan. 26, 2001

Related U.S. Patent Documents

Reissue of:
(64) Patent No.: 6,053,929
Issued: Apr. 25, 2000
Appl. No.: 09/273,677
Filed: Mar. 22, 1999

U.S. Applications:
(63) Continuation-in-part of application No. 09/052,588, filed on Mar. 31, 1998, now Pat. No. 5,938,676, which is a continuation-in-part of application No. 08/666,734, filed on Jun. 18, 1996, now Pat. No. 5,938,675, which is a continuation-in-part of application No. 08/376,065, filed on Jan. 20, 1995, now Pat. No. 5,527,329, which is a continuation of application No. 08/163,938, filed on Dec. 8, 1993, now abandoned.

(51) Int. Cl.
*A61B 17/32* (2006.01)

(52) U.S. Cl. ..... 606/167; 30/2; 30/151; 30/335

(58) Field of Classification Search ..... 606/167–185; 30/2, 286, 329, 151, 162, 320, 335
See application file for complete search history.

(56) References Cited

U.S. PATENT DOCUMENTS 2,552,945 A * 5/1951 Eaton et al. ..... 30/162
(Continued)

FOREIGN PATENT DOCUMENTS

DE 37 22 899 A1 7/1987
(Continued)

*Primary Examiner* — Anhtuan T Nguyen
*Assistant Examiner* — Kathleen Sonnett
(74) *Attorney, Agent, or Firm* — Price, Heneveld, Cooper, DeWitt & Litton, LLP

(57) ABSTRACT

A surgical scalpel includes an elongate handle defining a longitudinal axis and having a proximal end and a distal end. The scalpel has a cartridge removably mounted to the handle that has a blade holder with a proximal end and a distal end. There is a blade fixedly attached to blade holder disposed so that the blade projects distally outwardly when the cartridge is mounted on the handle. The cartridge also has a shield with a proximal end, a distal end and a bottom mounted onto the blade holder. The shield is slidably movable between a distal position where the shield substantially prevents inadvertent access to the blade and a proximal position where the shield substantially surrounds a portion of the handle and the blade is exposed for use. The cartridge is releasably mountable to the handle and has elements for substantially preventing movement of the shield with respect to the blade holder unless the cartridge is mounted on the handle. The cartridge further including elements for substantially preventing an inadvertent movement of the shield to the proximal position thereby to expose the blade as the cartridge is being mounted to the handle.

56 Claims, 44 Drawing Sheets

U.S. PATENT DOCUMENTS

| | | | | |
|---|---|---|---|---|
| 2,735,176 | A | | 2/1956 | Costin ..... 30/162 |
| 2,885,780 | A | | 5/1959 | Campbell ..... 30/164.9 |
| 2,968,489 | A | | 1/1961 | Doniger ..... 279/48 |
| 3,025,598 | A | | 3/1962 | Nissen ..... 30/162 |
| 3,657,812 | A | | 4/1972 | Lee ..... 30/162 |
| 3,793,726 | A | | 2/1974 | Schrank ..... 30/151 |
| 3,905,101 | A | | 9/1975 | Shepherd ..... 30/162 |
| 3,906,626 | A | | 9/1975 | Riuli ..... 30/162 |
| 4,091,537 | A | | 5/1978 | Stevenson, Jr. ..... 30/286 |
| 4,318,473 | A | | 3/1982 | Sandel ..... 206/370 |
| 4,375,218 | A | | 3/1983 | DiGeronimo ..... 128/303.17 |
| 4,414,974 | A | | 11/1983 | Dotson et al. ..... 128/305 |
| 4,491,132 | A | | 1/1985 | Aikins ..... 128/305 |
| 4,523,379 | A | | 6/1985 | Osterhout et al. ..... 30/151 |
| 4,660,287 | A | | 4/1987 | Decker ..... 30/339 |
| 4,663,846 | A | | 5/1987 | Takayama ..... 30/162 |
| 4,735,202 | A | | 4/1988 | Williams ..... 128/305 |
| 4,805,304 | A | | 2/1989 | Knoop ..... 30/162 |
| 4,823,457 | A | | 4/1989 | Prochaska ..... 29/509 |
| 4,844,070 | A | | 7/1989 | Dee ..... 128/305 |
| 4,884,569 | A | | 12/1989 | Fedorov et al. ..... 128/305 |
| 4,949,458 | A | | 8/1990 | Davis et al. ..... 30/162 |
| 5,055,106 | A | | 10/1991 | Lundgren ..... 606/167 |
| 5,071,418 | A | | 12/1991 | Rosenbaum ..... 606/42 |
| 5,071,426 | A | | 12/1991 | Dolgin et al. ..... 606/167 |
| D327,125 | S | | 6/1992 | Iten ..... D24/146 |
| 5,141,517 | A | | 8/1992 | Shutt ..... 606/167 |
| D329,699 | S | | 9/1992 | Schutte et al. ..... D24/147 |
| D330,082 | S | | 10/1992 | Schutte et al. ..... D24/147 |
| 5,201,748 | A | | 4/1993 | Newman et al. ..... 606/167 |
| 5,207,696 | A | | 5/1993 | Matwijcow ..... 606/167 |
| 5,250,063 | A | | 10/1993 | Abidin et al. ..... 606/167 |
| 5,250,064 | A | | 10/1993 | Schneider ..... 606/167 |
| 5,254,128 | A | * | 10/1993 | Mesa ..... 606/167 |
| 5,275,606 | A | | 1/1994 | Abidin et al. ..... 606/167 |
| 5,292,329 | A | * | 3/1994 | Werner ..... 606/167 |
| 5,299,357 | A | | 4/1994 | Wonderley et al. ..... 30/339 |
| 5,309,641 | A | | 5/1994 | Wonderley et al. ..... 30/339 |
| 5,312,429 | A | | 5/1994 | Noack ..... 606/167 |
| 5,330,493 | A | * | 7/1994 | Haining ..... 606/167 |
| 5,330,494 | A | | 7/1994 | van der Westhuizen et al. ..... 606/167 |
| 5,342,379 | A | | 8/1994 | Volinsky ..... 606/167 |
| 5,363,958 | A | | 11/1994 | Horan ..... 206/356 |
| 5,370,654 | A | | 12/1994 | Abidin et al. ..... 606/182 |
| 5,411,512 | A | | 5/1995 | Abidin et al. ..... 606/167 |
| 5,417,704 | A | | 5/1995 | Wonderley ..... 606/167 |
| 5,449,068 | A | | 9/1995 | Gharibian ..... 206/355 |
| 5,481,804 | A | | 1/1996 | Platts ..... 30/162 |
| 5,571,127 | A | | 11/1996 | DeCampli ..... 606/167 |
| 5,599,351 | A | * | 2/1997 | Haber et al. ..... 606/167 |
| 5,620,454 | A | | 4/1997 | Pierce et al. ..... 606/167 |
| 5,662,669 | A | | 9/1997 | Abidin et al. ..... 606/167 |
| 5,683,407 | A | | 11/1997 | Jolly et al. ..... 606/181 |
| 5,741,289 | A | | 4/1998 | Jolly et al. ..... 606/181 |
| 5,752,968 | A | | 5/1998 | Jolly et al. ..... 606/167 |
| 5,792,162 | A | | 8/1998 | Jolly et al. ..... 606/167 |
| 5,827,309 | A | | 10/1998 | Jolly et al. ..... 606/167 |
| 5,941,892 | A | * | 8/1999 | Cohn et al. ..... 606/167 |

FOREIGN PATENT DOCUMENTS

| | | |
|---|---|---|
| WO | WO 97/34535 | 9/1997 |

* cited by examiner

SURGICAL SCALPEL

Matter enclosed in heavy brackets [ ] appears in the original patent but forms no part of this reissue specification; matter printed in italics indicates the additions made by reissue.

This application is a Continuation-In-Part of U.S. patent application Ser. No. 09/052,588 filed Mar. 31, 1998, now U.S. Pat. No. 5,938,676 which is a Continuation in Part of U.S. patent application Ser. No. 08/666,734 filed Jun. 18, 1996, now U.S. Pat. No. 5,938,675 which is a Continuation-In-Part of U.S. patent application Ser. No. 08/376,065 filed Jan. 20, 1995 that is now U.S. Pat. No. 5,527,329, issued Jun. 18, 1996, which is a Continuation Application of U.S. patent application Ser. No. 08/163,938 filed on Dec. 8, 1993, abandoned.

The field of the invention is surgical cutting instruments. Conventional surgical instruments provide a significant potential for harm to surgeons, nurses and other support personnel. In the operating room, various surgical instruments are quickly passed by hand. The rapid handling of such instruments with exposed sharp edges can lead to accidental cuts of puncture wounds. Surgical gloves may also be inadvertently punctured leading to loss of glove integrity further increasing the risk of infection to a surgeon, nurse or other medical personnel.

Previous attempts to guard against inadvertent cuts or punctures led to the development of retractable blade guards. Some of the earliest versions were simply retractable bladed knives used in various industries outside the medical field. These blade guards generally required two hands to operate, i.e., one hand to manipulate the blade and a second hand to secure the blade guard by turning a threaded screw. Other conventional devices having spring loaded moving parts or tabs that clipped into notches on a hollow tubed sheathing device, were not practical for surgical use because they did not provide a good grip or "feel" for the blade.

SUMMARY

A surgical scalpel includes an elongate handle defining a longitudinal axis and having a proximal end and a distal end. The scalpel has a cartridge removably mounted to the handle that has a blade holder with a proximal end and a distal end. There is a blade fixedly attached to blade holder disposed so that the blade projects distally outwardly when the cartridge is mounted on the handle. The cartridge also has a shield with a proximal end, a distal end and a bottom mounted onto the blade holder. The shield is slidably movable between a distal position where the shield substantially prevents inadvertent access to the blade and a proximal position where the shield substantially surrounds a portion of the handle and the blade is exposed for use. The cartridge is releasably mountable to the handle and has elements for substantially preventing movement of the shield with respect to the blade holder unless the cartridge is mounted on the handle. The cartridge further includes elements for substantially preventing an inadvertent movement of the shield to the proximal position, thereby to expose the blade as the cartridge is being mounted to the handle.

The scalpel of the invention provides practitioners with a scalpel that has the feel and weighting of a traditional reusable scalpel with the benefits of a fresh blade and a shield that substantially prevents inadvertent access to the sharp blade and that is intuitively movable from the distal position where the blade is protected to the proximal position to expose the blade. The shield of the scalpel of the invention is releasable from the proximal position by the practitioner's direct downward pressure on a digital activation section. The shield includes ergonomic grips to direct the practitioner's hand to a position for mounting the cartridge on the handle where it is unlikely that there will be inadvertent release of the shield for movement from the [proximal] *distal* position where the blade is protected to the [distal] *proximal* position where the blade is exposed. The replaceable cartridge that includes the blade allows the personnel charged with arming and disarming the scalpel to handle only a protected blade and substantially prevents operating room personnel from being exposed to the blade during set-ups and transfers of equipment during procedures and substantially prevents exposures to used blades during disarming and clean-up procedures.

BRIEF DESCRIPTION OF THE DRAWINGS

In the drawings, wherein similar reference numbers denote similar elements throughout the several views:

FIG. 40b is a diagram of the cantilever portion of the shield of the embodiment shown in FIGS. 25-36c, analogous to FIG. 40a;

DETAILED DESCRIPTION

Figure 1:
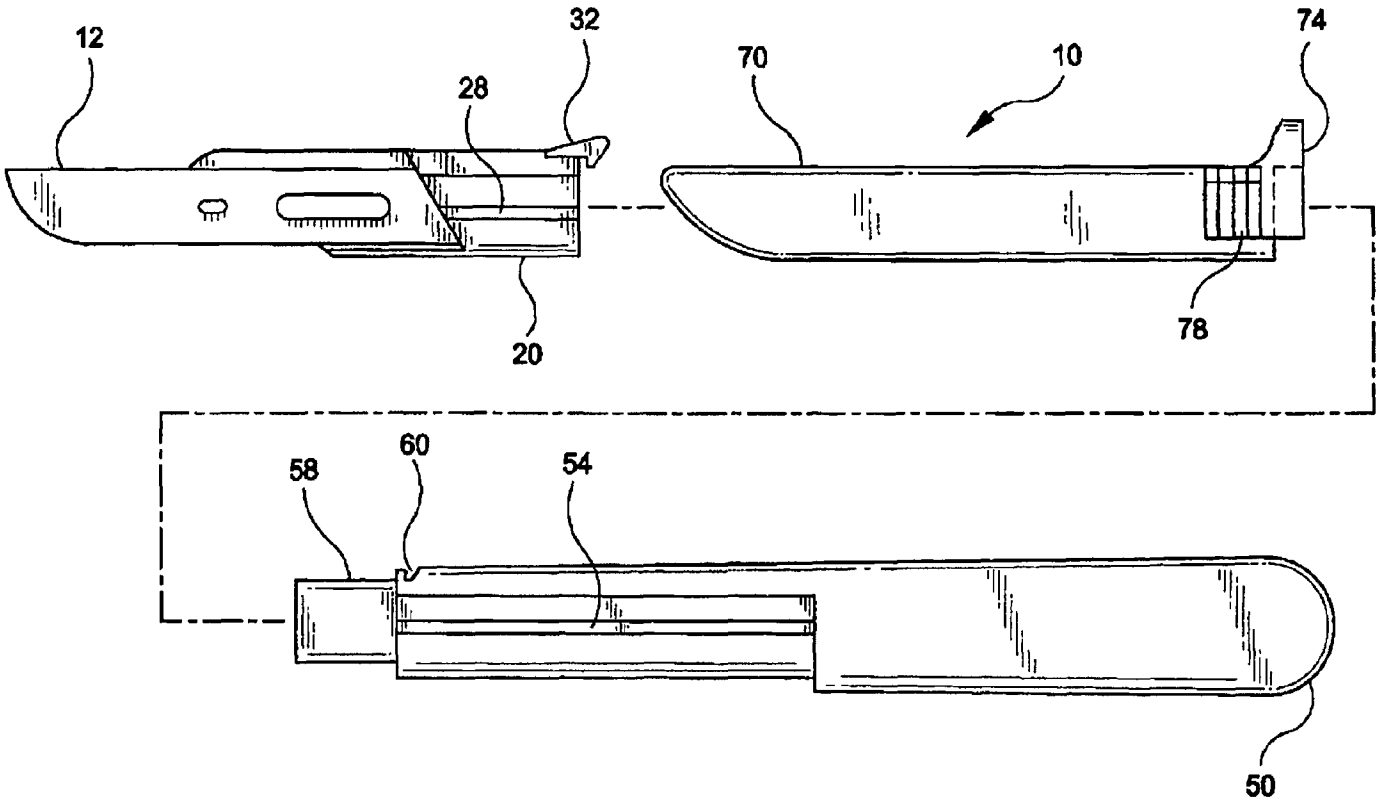
FIG. 1 is an exploded side elevation view of a preferred embodiment of the present scalpel.
Figure 2A:
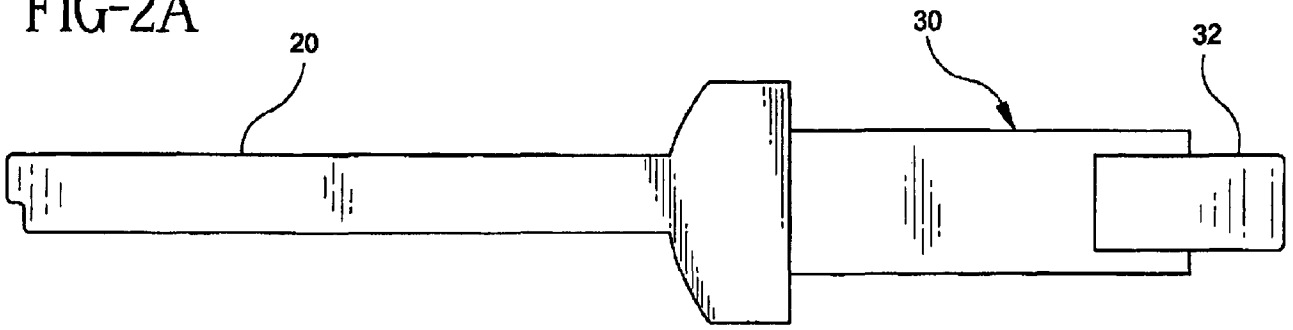
FIG. 2a is a top view of the blade holder.
Figure 2B:
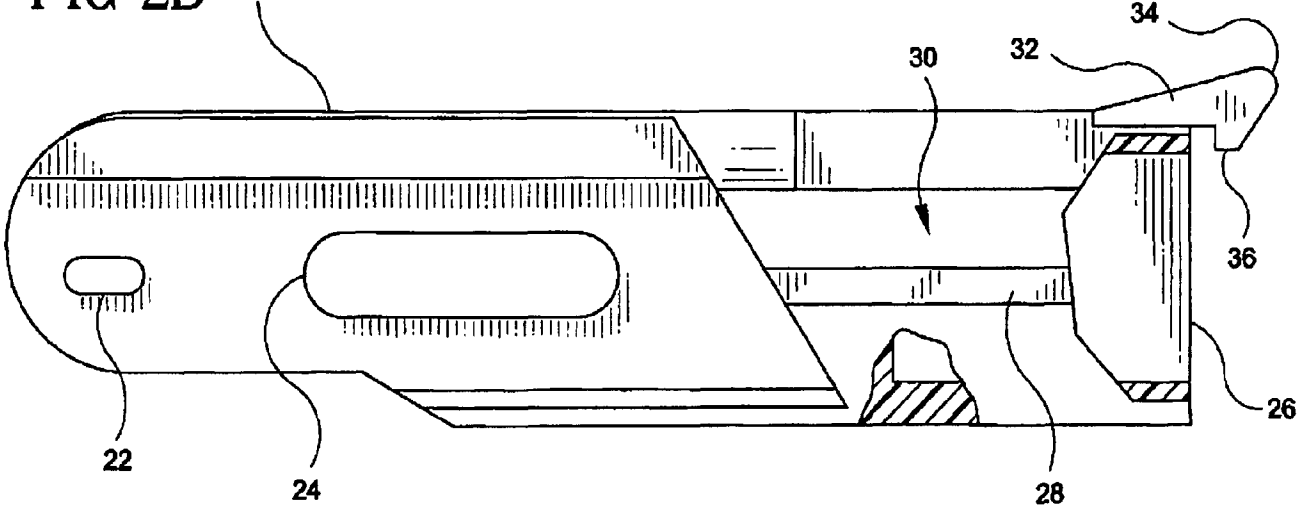
FIG. 2b is a side elevation view of the blade holder illustrating the position of the hook in the preferred embodiment and illustrating a partial section view of the attachment slot.
Figure 2D:
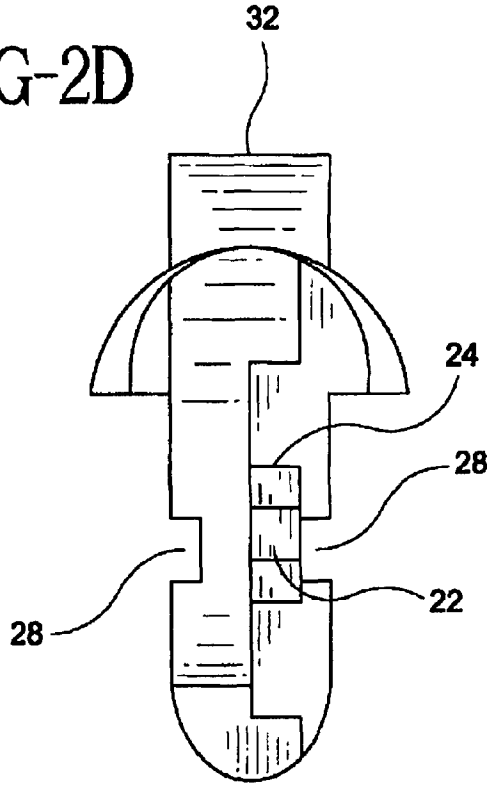
FIG. 2d is a front end view thereof.
Figure 2C:
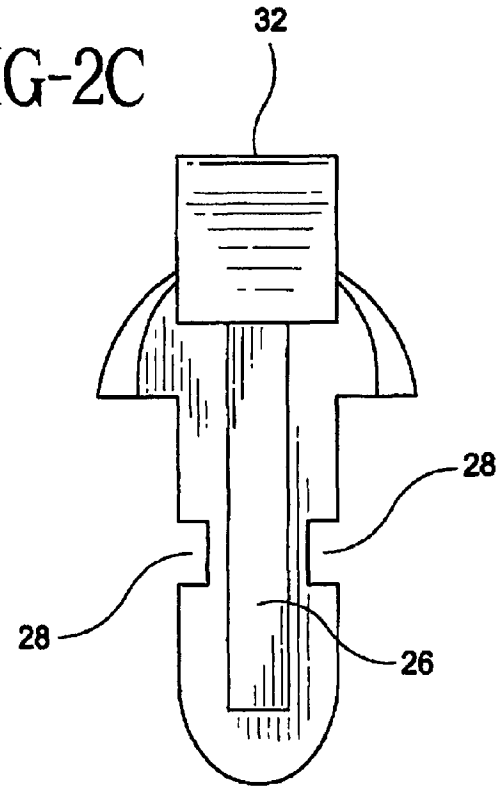
FIG. 2c is a back end view of the blade holder showing the hook and the attachment slot.

Turning in detail to the FIGS. 1-15, the surgical scalpel 10 is first shown in FIG. 1 with the blade 12 secured to the blade holder 20. The scalpel 10 is gripped by the [hand] *handle* 50 which has a preferably contoured elongated grip portion 52. As is shown in FIGS. 2a and 2b, adjacent the frond end of the blade holder 20 are two tabs 22 and 24 for securing the blade 12 to the blade holder 20 by inter locking with respective openings on the blade 12. Adjacent the back end of the blade holder 20 is the attachment slot 26 shown as a female end connection. Channels 28 are positioned longitudinally on opposite sides of the blade holder 20 along a channel section 30 o the blade holder 20.

A hook 32 is cantilevered from the back end of the blade holder 20. The hook 32 can resiliently flex upwardly and downwardly to engage the handle 50. The cantilevered end of the hook 32 has an inclined aft surface 34 and a protrusion 36 which is adapted to engage a complementary shaped [grooved 50] *groove 60* on the handle 50 when the blade holder 20 mates with the handle 50.

Figure 3A:
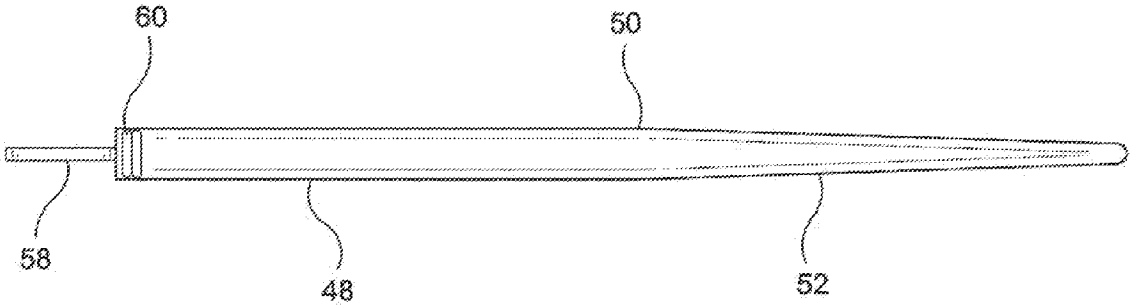
FIG. 3a is a top view of the handle shown in FIG. 1.
Figure 3B:
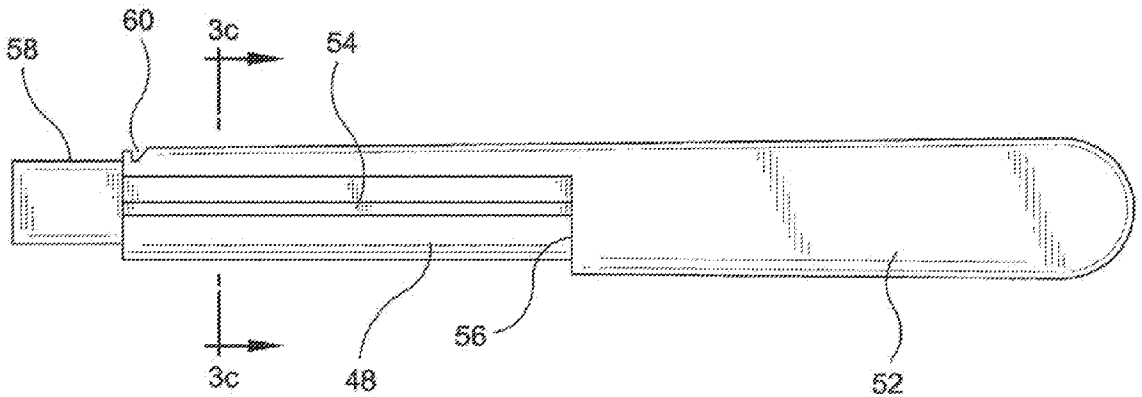
FIG. 3b is a side elevation view of the handle illustrating the groove and a male end attachment flange.

Referring now to FIGS. 3a and 3b, a pair of guide channels 54 are provided on opposite sides of the guide channel section 48 of the handle 50 in front of the grip portion 52. The guide channels 54 terminate at detents where the guide channel section 48 adjoins the grip portion 52.

Figure 3D:
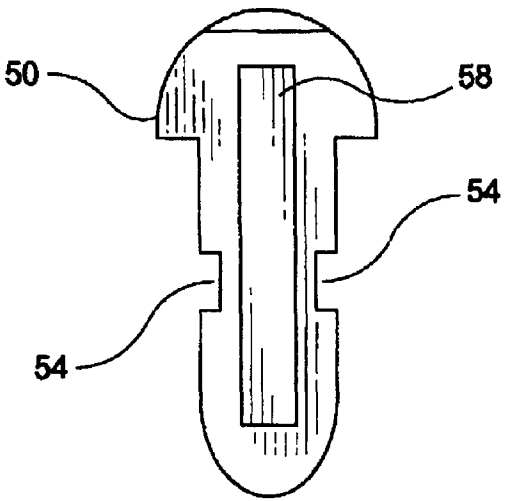
FIG. 3d is a front end view of the handle.
Figure 3C:
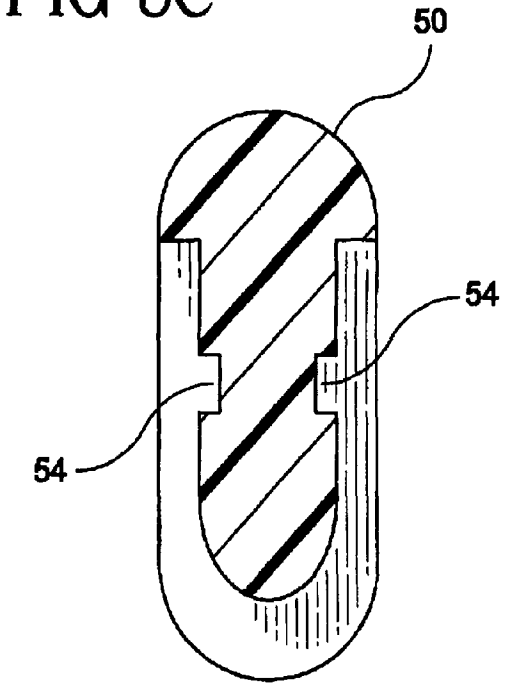
FIG. 3c is a section view taken along line 3c-3c of FIG. 3b.
Figure 4A:
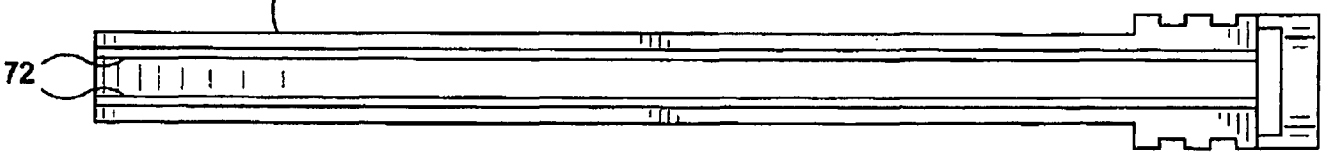
FIG. 4a is a top view of the sleeve.
Figure 4B:
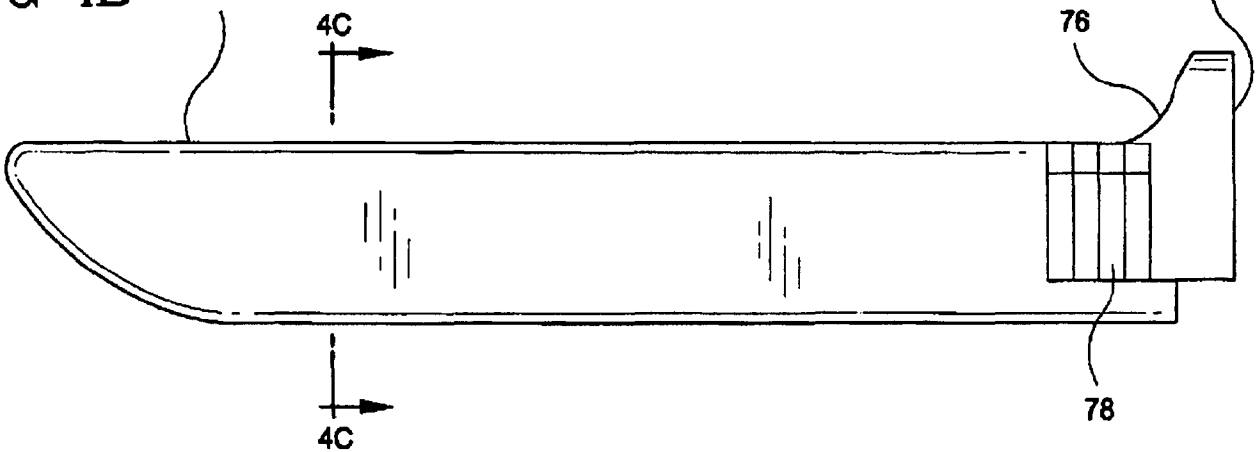
FIG. 4b is a side elevation view thereof.
Figure 4D:
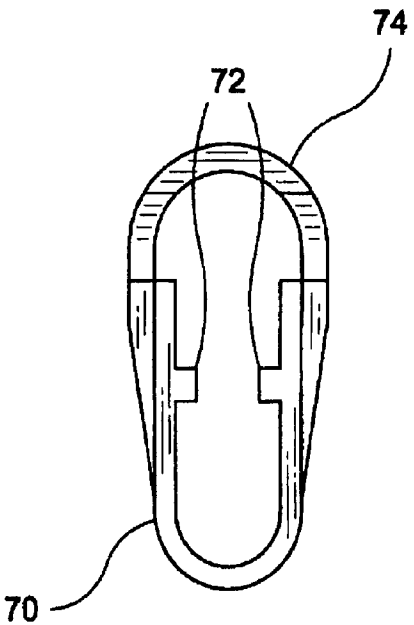
FIG. 4d is a front end view of the sleeve showing the arch.
Figure 4C:
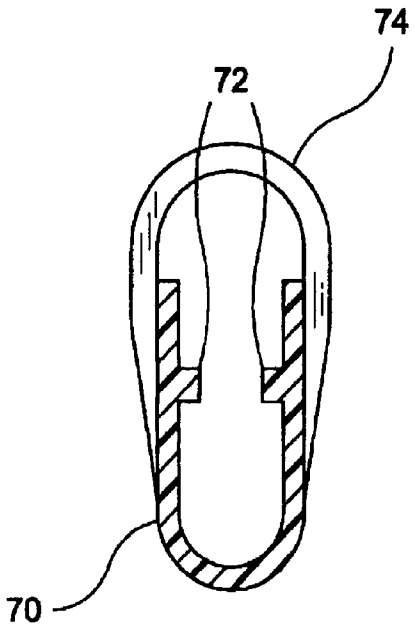
FIG. 4c is a section view of the sleeve taken along line 4c-4c of FIG. 4b.

An attachment flange 58 (shown as a male ended attachment is joined to the front end of the guide channel section 48. As shown in FIGS. 3b and 3d, the attachment flange 58 is generally rectangular in cross section, although other configurations are possible, and is adapted to mate with the attachment slot 26 of the blade holder 20. A groove 60 at the forward end of the guide channel section 48 is shaped to mate with the hook 32.

Next referring to FIGS. 4a through 4d, the sleeve 70 is generally U-shaped in cross section having a closed bottom portion and an open upper portion. A pair of guide flanges 72 are positioned within the sleeve 70 spans between the two sides of the sleeve 70. The arch 74 preferably has a radiused front surface 76.

Figure 5A:
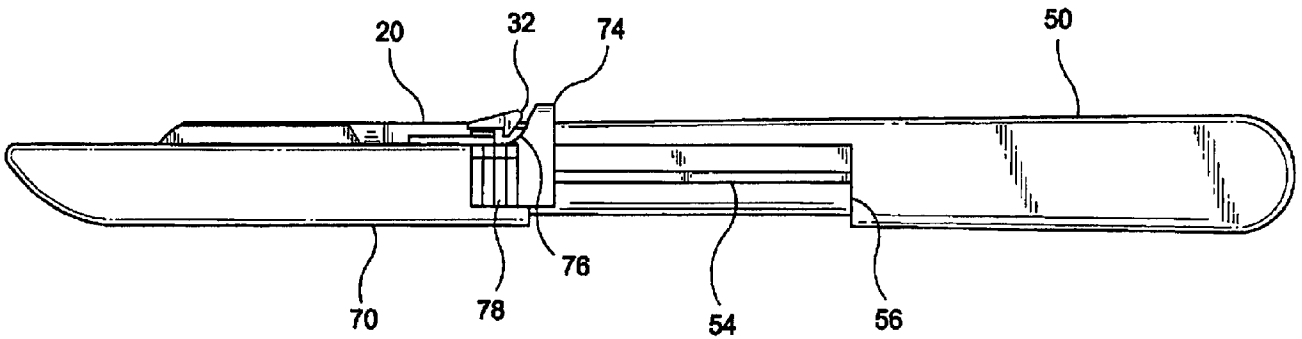
FIG. 5a is a side elevation view of the assembled scalpel with the sleeve positioned in an extended position.

The sleeve 70 preferably has a digit engaging portion 78 adjacent to the arch 74 having a series of ribs forming a thumb rest. [the] *The* digit engaging portion 78 improves the surgeon's "feel" for the sleeve 70 when the sleeve 70 slides along the guide channels 28 and 54 by hand or thumb pressure. FIG. 5a shows an assembled scalpel 10 with the sleeve 70 in a forward position to cover [of sheath] the blade 12. The forward movement of the sleeve 70 is guided by the guide flanges 72 that travel along the guide channels 28 and 54. With the sleeve 70 moved fully forward, the radiused surface 76 contacts the hook 32 to stop additional forward movement.

Additional forward movement by the sleeve 70 toward the extended position as guided by the user's hand will cause the arch 74 to lift the hook 32 out of the groove 60 for removal of the blade holder 20 from the handle 50. This allows the sleeve 70 and blade holder to be disassembled as a unit from the handle 50 while the blade 12 is sheathed by the sleeve 70, thus minimizing the risks of inadvertent cuts. The blade 12, blade holder and sleeve 70 may then be disposed of. the handle may advantageously be reused.

Figure 5B:
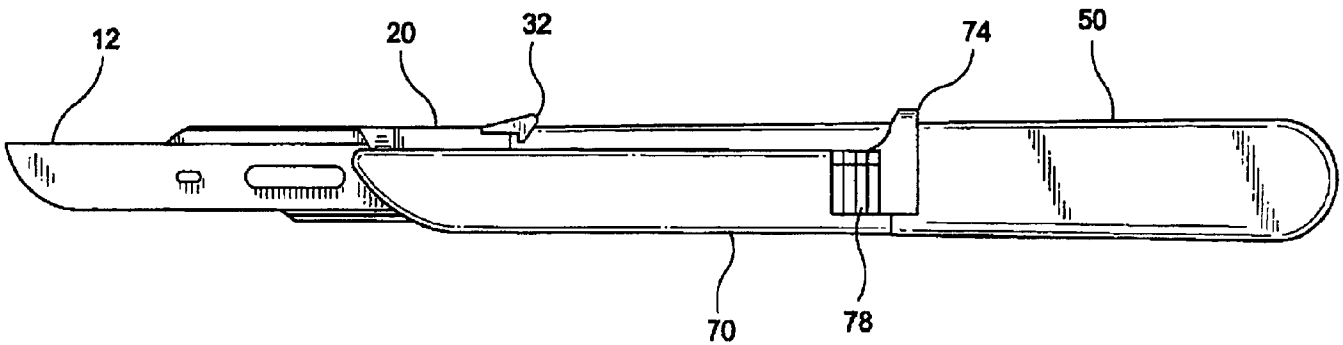
FIG. 5b is an elevation view thereof with the sleeve in a retracted position.
Figure 5C:
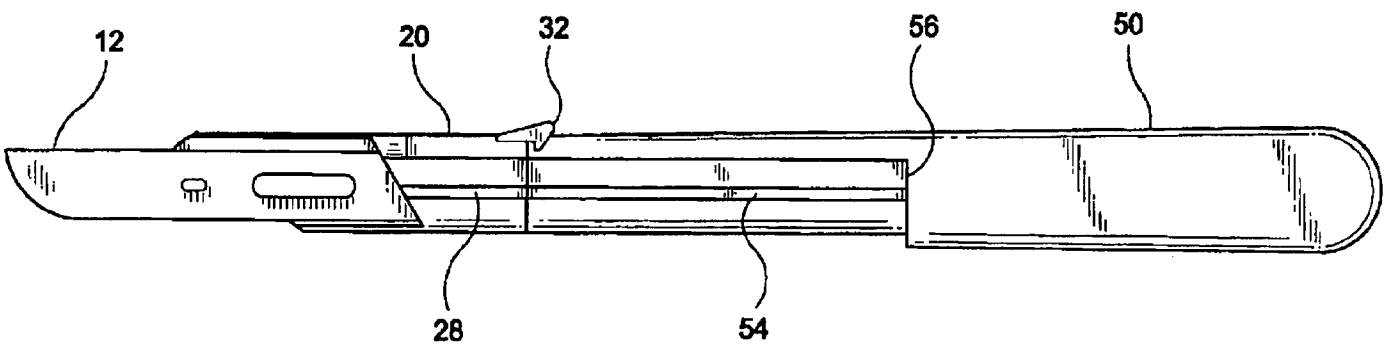
FIG. 5c is a side elevation view with the sleeve removed.

FIG. 5b shows the sleeve 70 moved to the fully retracted position with the back end of the sleeve 70 abutting the detents 56 to fully expose the blade 12. the user may utilize the digit engaging portion 781 on the sleeve 20 to improve fingertip control of the longitudinal front to back movement of the sleeve 70. FIG. 5c shows the sleeve 70 removed from the handle 50 (for purposes of illustration).

Figure 6:
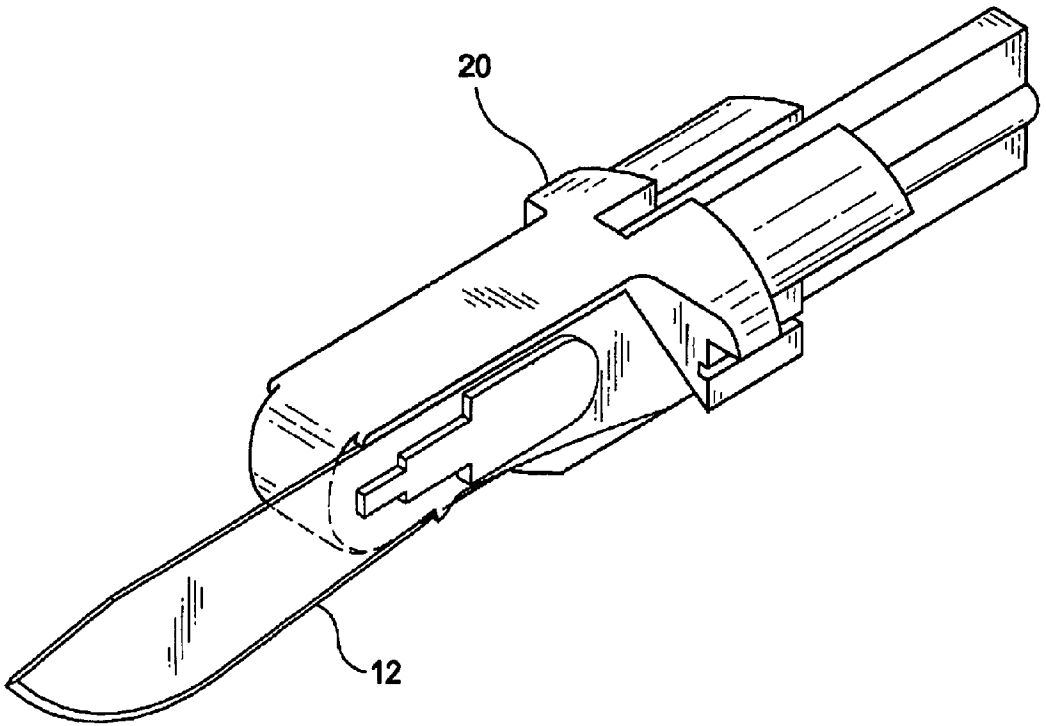
FIG. 6 shows a perspective *view* of an alternative embodiment of the blade holder with the blade attached.
Figure 7:
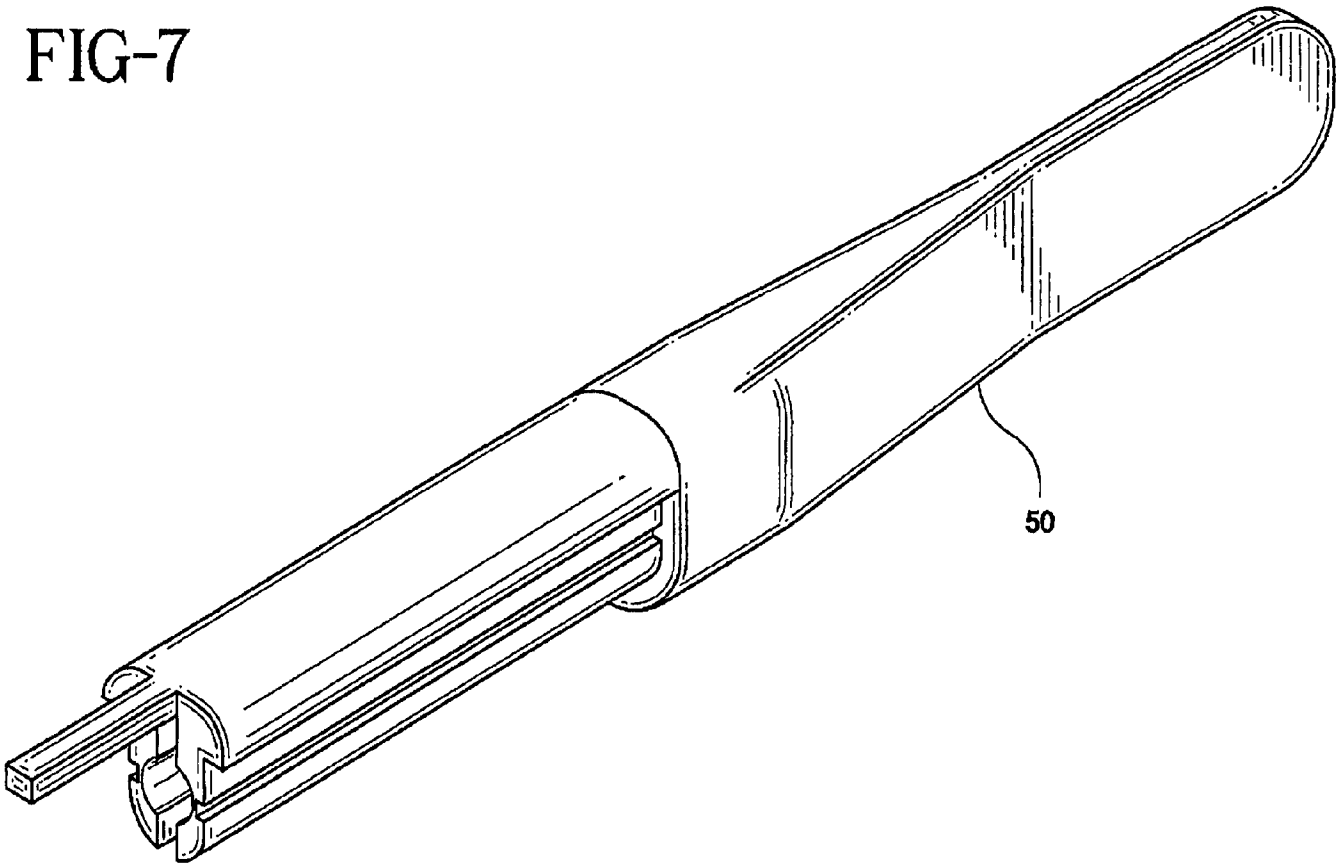
FIG. 7 is a perspective view of an alternative embodiment of the handle.
Figure 8:
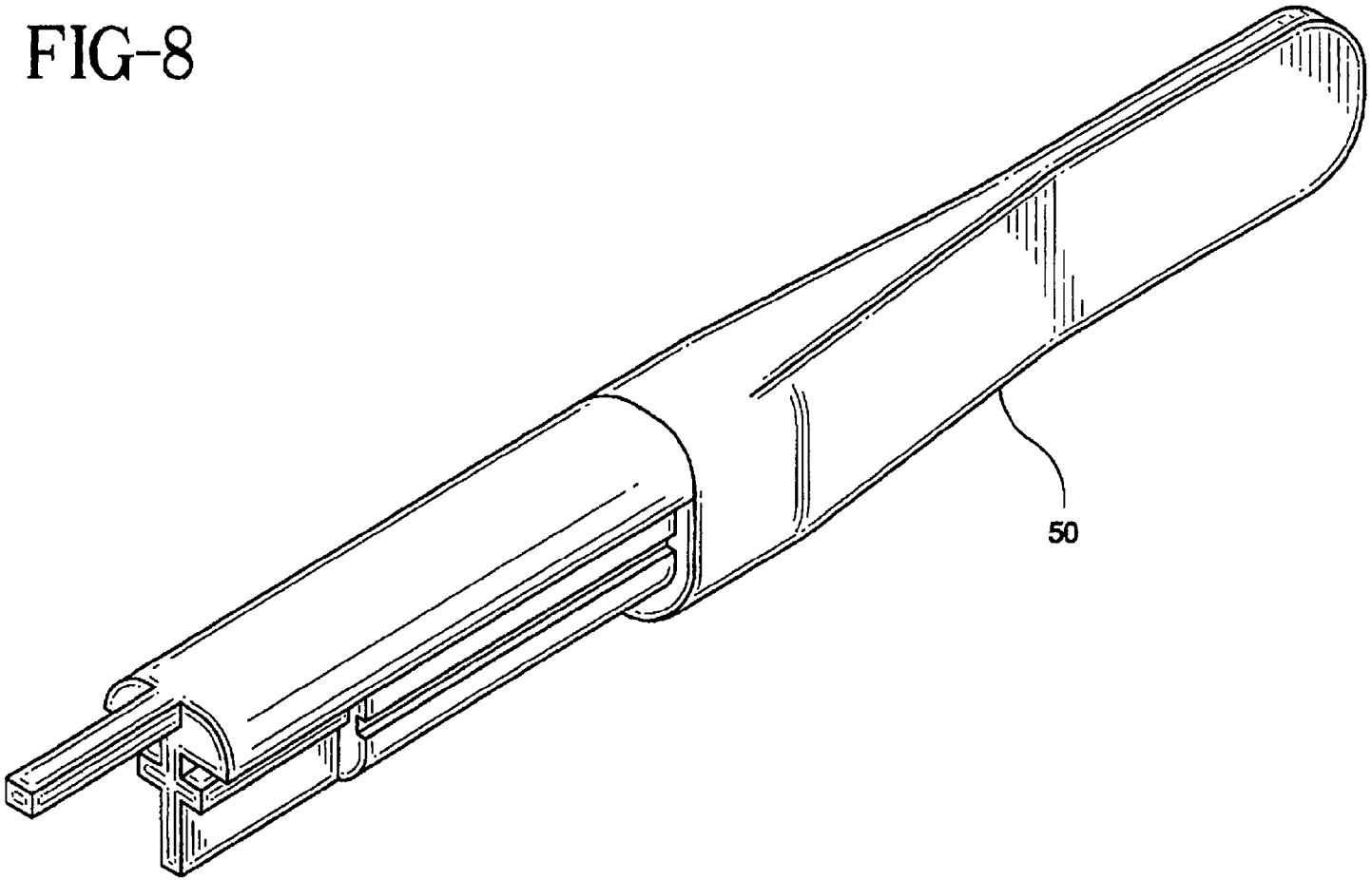
FIG. 8 is a perspective view of a second alternative embodiment of the handle.
Figure 9:
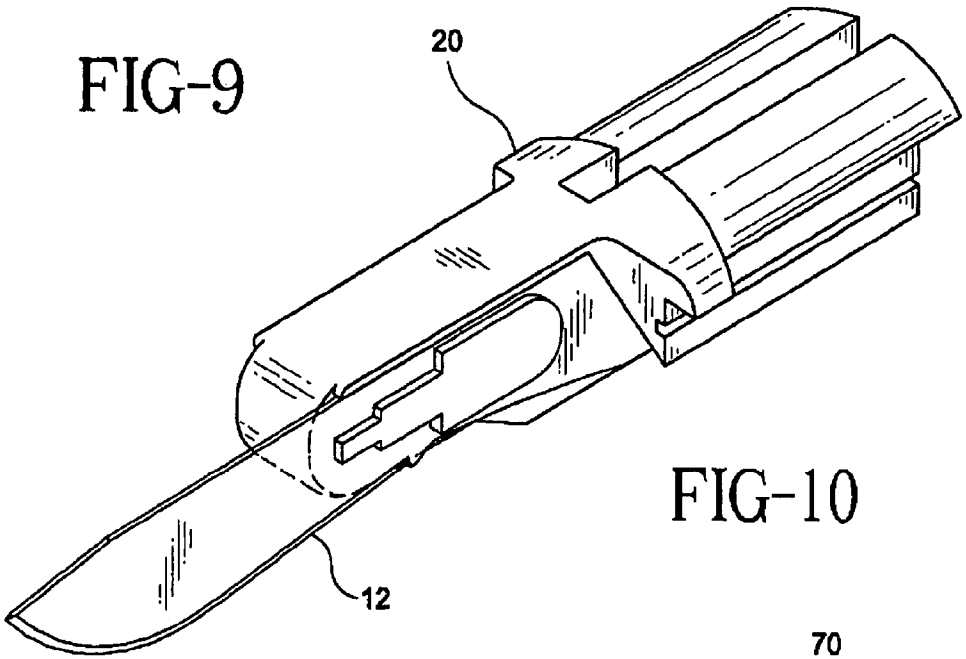
FIG. 9 is a perspective view of an alternative embodiment of the blade holder having a female end connection.
Figure 10:
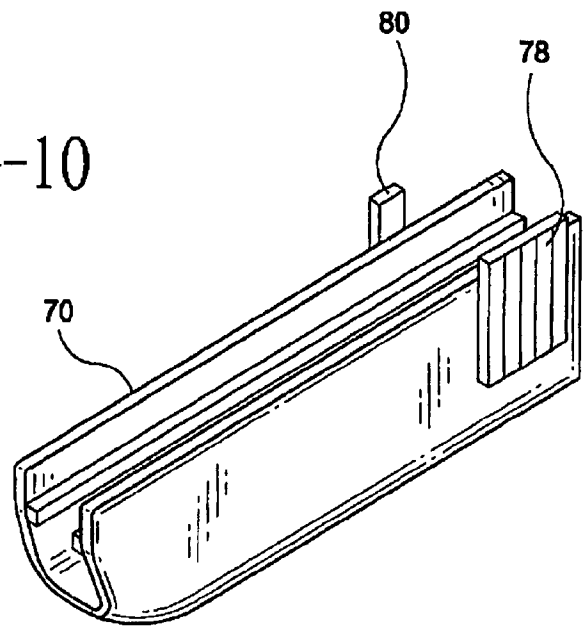
FIG. 10 is a perspective view of an alternative embodiment of the sleeve.

FIG. 6 illustrates an embodiment of the blade holder 20 with both a male ended attachment and a female ended slot. FIG. 7 shows an embodiment of the handle 50 which mates with the blade holder 20 shown in FIG. 6. An alternative embodiment of the handle 50 is also shown in FIG. 8 with male ended connections. An embodiment of the blade holder 20 which mates with the handle 50 of FIG. 8 is further shown in FIG. 9 with an outline of the attached blade 12. An alternative embodiment of the sleeve 70 is shown in FIG. 10 which illustrates a stop tab 80 which may be utilized to stop forward longitudinal sliding of the sleeve 70. An inclined digit engaging portion 78 is illustrated and may be used to facilitate use as a thumb rest for the operation surgeon.

Figure 11:
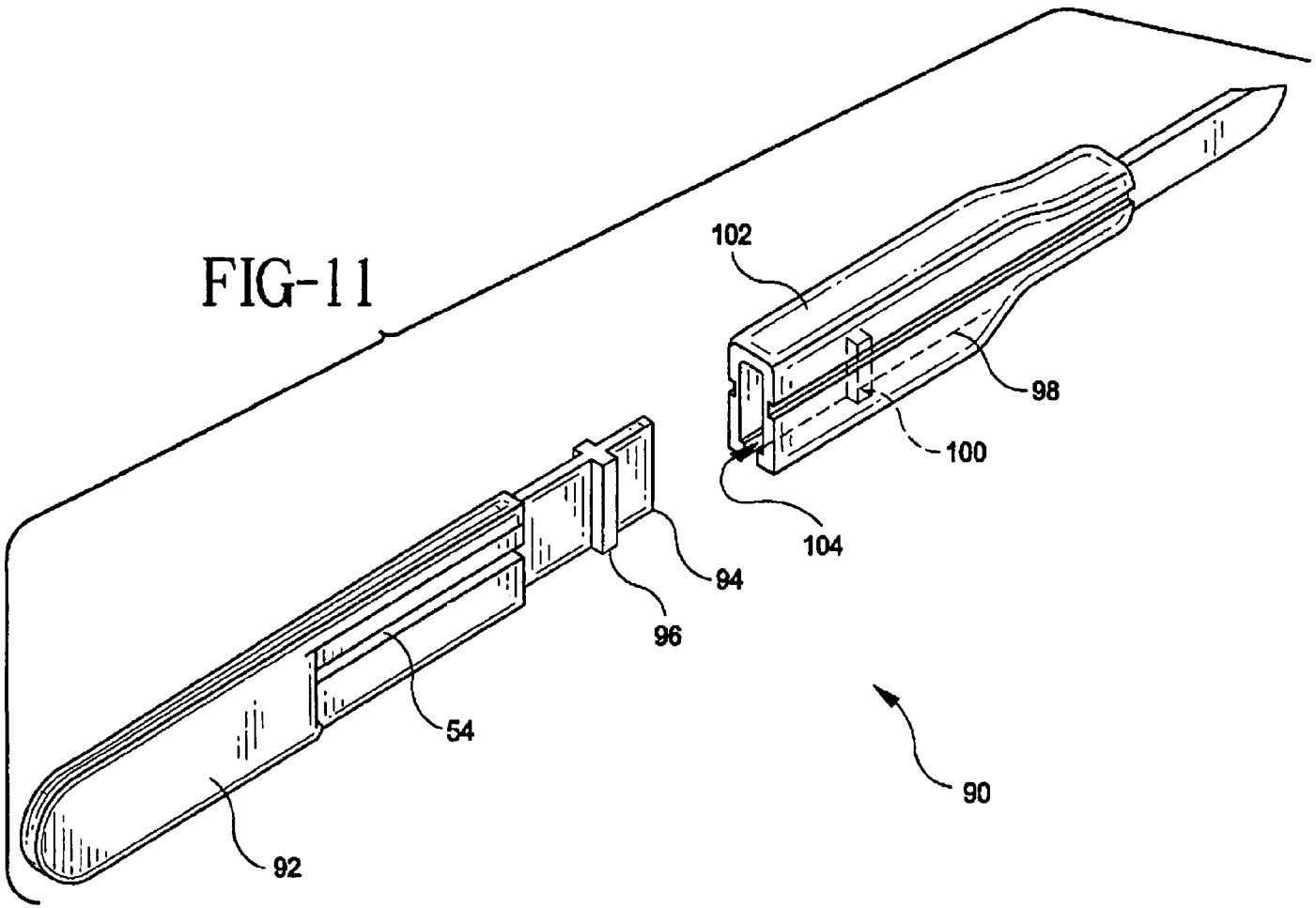
FIG. 11 is a perspective view of an alternative embodiment with the blade holder attached to the handle using vertical slots and tabs.

In an alternative embodiment 90 as shown in FIG. 11, a handle 92 has a flange 94 with vertical tabs or protrusions 96. A blade holder 98 has internal vertical slots 100 adapted to vertically slide down over the tabs 96, from above. A sleeve 102 is secured to the blade holder 98, as described above with reference to FIGS. 1-5. The sleeve 102 has a slot 104 at the back end of its lower surface. In use, the blade holder 98 is attached to the handle 92 by engaging the vertical tabs 96 into the vertical slots 100, by sliding the blade holder 98 down onto the handle 92 from above. the slot 104 in the bottom of the sleeve 102 provides sufficient clearance for the protruding vertical tabs 96.

Figure 12:
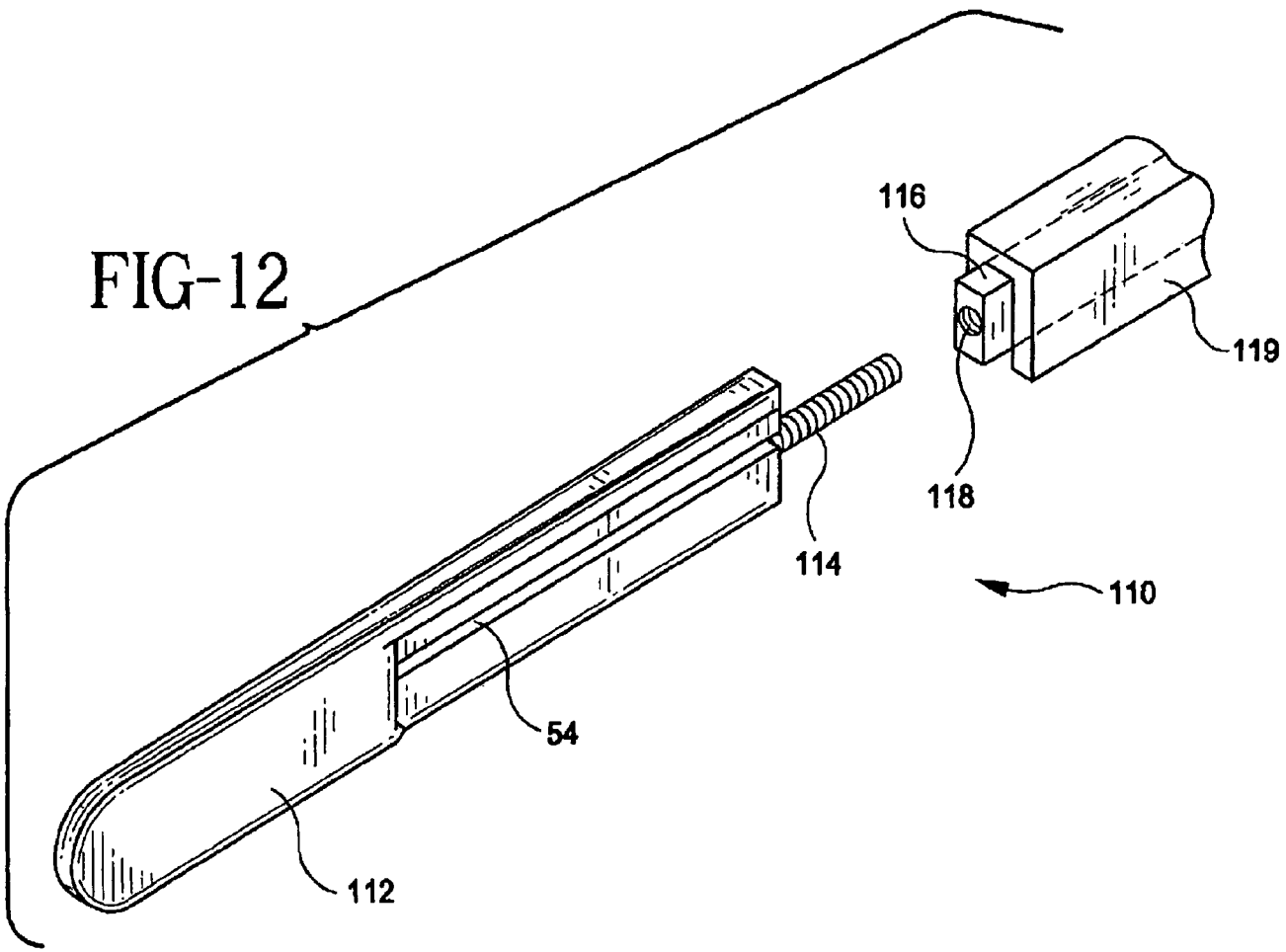
FIG. 12 is an exploded partial perspective view of an alternative embodiment with the blade holder threaded onto the handle.

Turning to FIG. 12, a surgical scalpel 110 has a handle 112 with a threaded stud 114 at its front end. The stud 114 threads into a threaded hole 118 at the back end of a blade holder 116. The threads on the stud 114 and in the threaded hole 118 are advantageously cut so that when the blade holder 116 bottoms out of the front end of the handle 112, the blade holder 116 will be properly vertically aligned. A sleeve 119 overlies the blade holder 116. The operation and design features of the surgical scalpels shown in FIGS. 11 and 12 are similar to the embodiment in FIGS. 1-5, except as described above.

Figure 14:
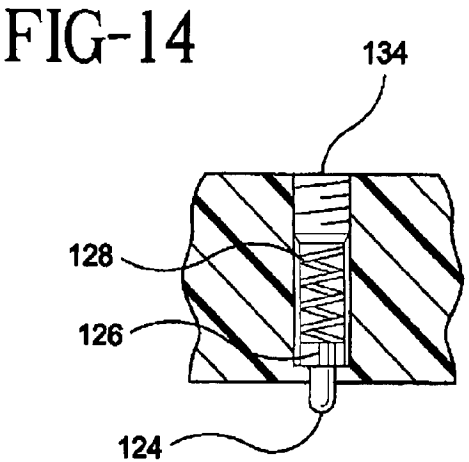
FIG. 14 is an enlarged section view of the locking button of FIG. 13.
Figure 13:
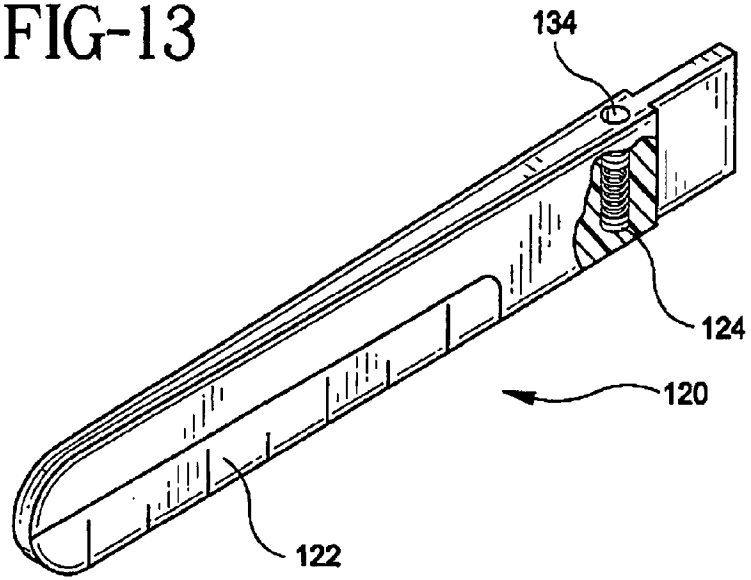
FIG. 13 is a perspective view in [part] *partial* section of an alternative handle embodiment having a button for locking the shield in position over the blade.
Figure 15:
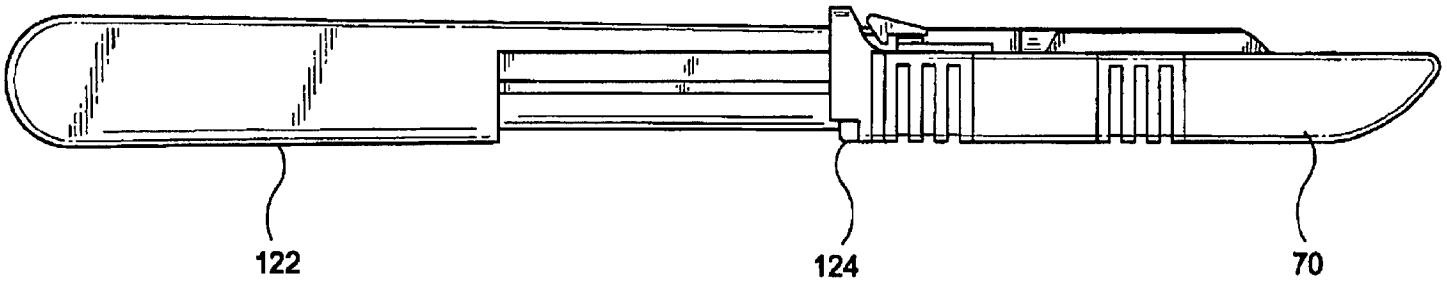
FIG. 15 is a side elevation view of the button of FIG. 14 locking the shield in its extended position.

As shown in FIG. 13 an alternative handle embodiment 122 has a locking button 124. As shown in FIG. 14, the locking button 124 has a shoulder 126 which fits within a bore 130 in the handle 122. A plug or set screw 134 at the top of the handle 122 retains a spring 128 in the bore 130, with the spring 128 biasing the locking button 124 to protrude out of the bottom surface of the handle 122. Referring to FIG. 15, with the shield 70 fully extended to cover the blade, 12, the locking button 124 protrudes out of the bottom of the handle 122. The sleeve 70 can not be retracted to expose the blade, without first pushing the locking button 124 up into the bore 130. Once the locking button is pushed up into the bore, the sleeve may be retracted, with the locking button sliding in the inside lower wall or surface of the sleeve. Accordingly, the locking button 124 helps to prevent inadvertent exposing of the blade 12. The locking button feature may be used on any of the surgical scalpel embodiment described above.

While a preferred embodiment of the present invention has been shown and disclosed in the drawings and specifications, alternate embodiments of the present invention would be apparent to the person of ordinary skill in the art and this application is intended to include those embodiments within the full breadth and scope of the claims. Moreover, the present invention need not include all of the features disclosed in the single embodiment but rather one or more features may be included.

While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. The scope of the invention is measured by the appended claims and their equivalents. In this disclosure, the term "proximal" refers to the portions of the device closest to the practitioner and the term "distal" refers to the portion of the device away from the practitioner.

Figure 16:
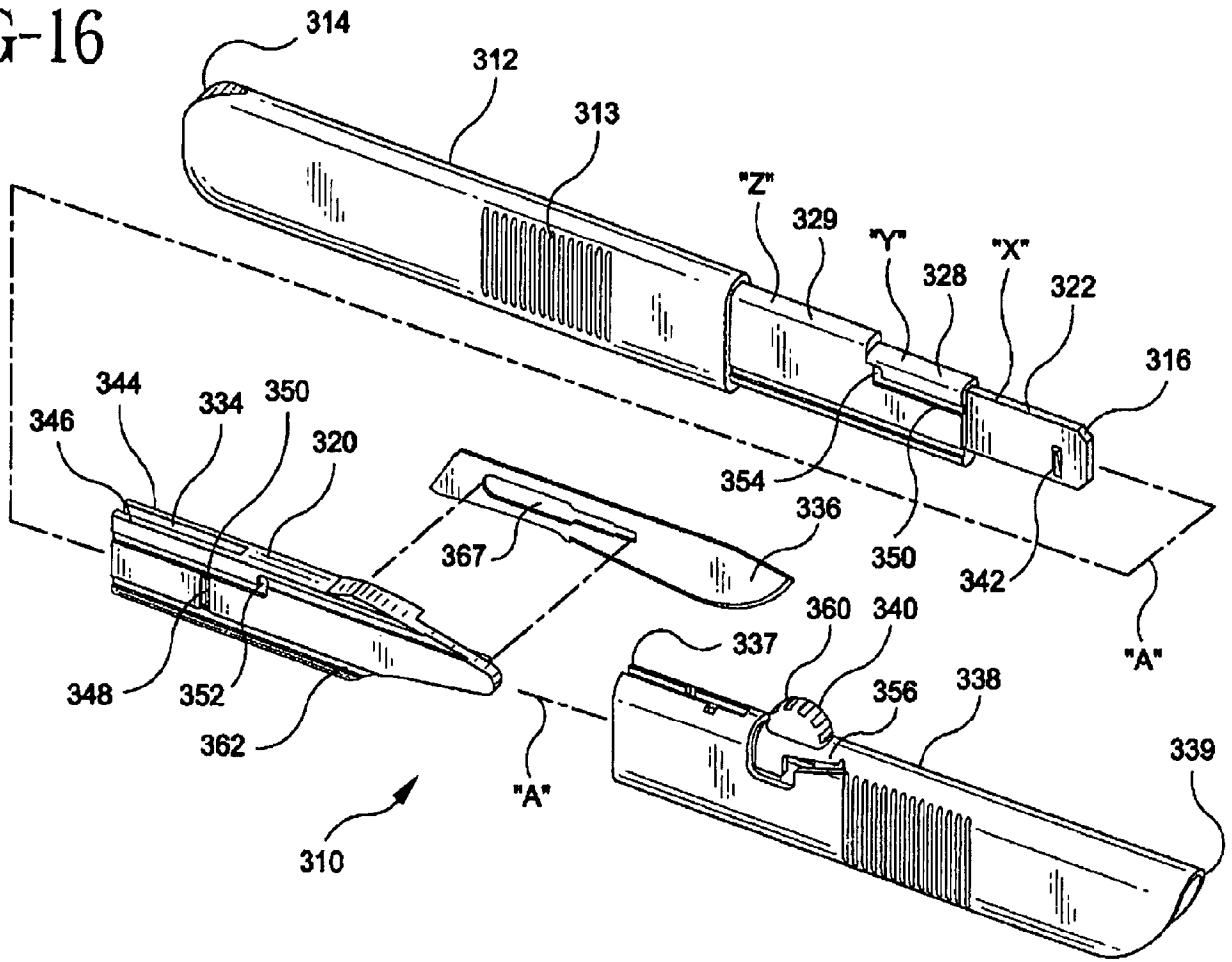
FIG. 16 is an exploded perspective view of another embodiment of the scalpel of the present invention.
Figure 17:
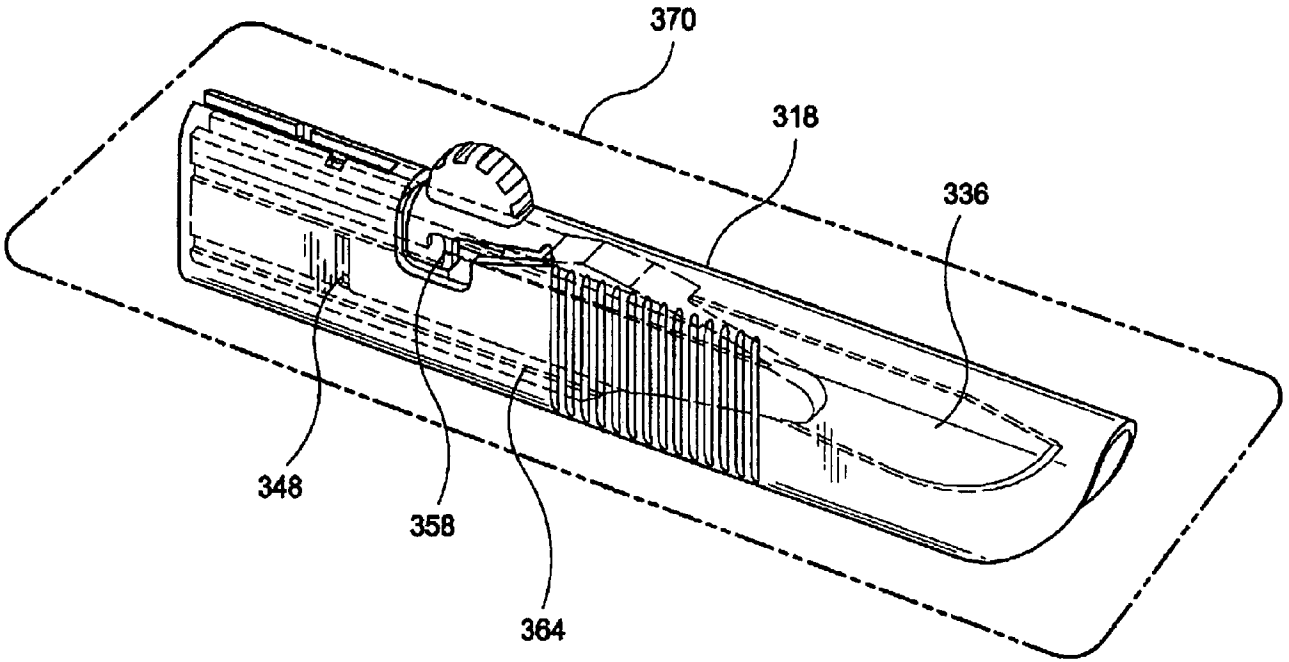
FIG. 17 is a schematic perspective view of the cartridge portion of the scalpel of FIG. 17.
Figure 18:
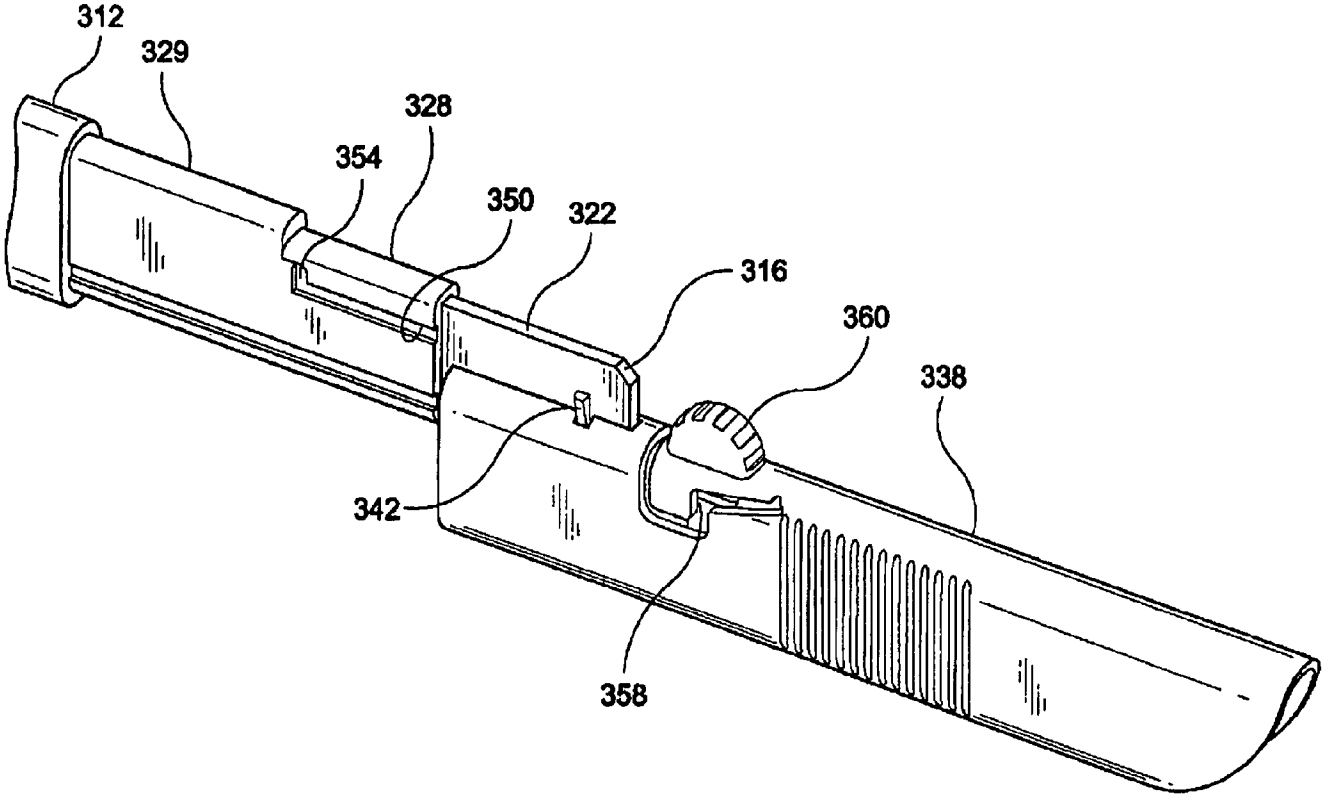
FIG. 18 is a partial perspective view of the cartridge being mounted to the handle [of] to form the scalpel of the invention.
Figure 19:
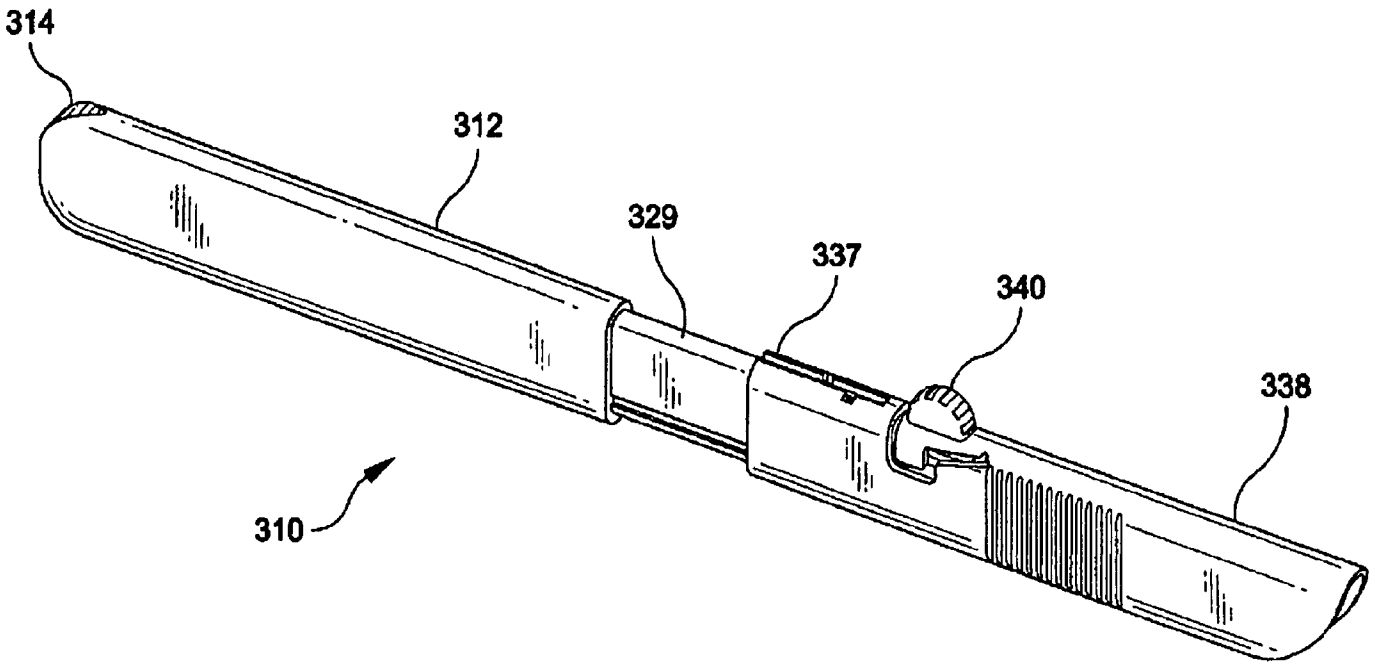
FIG. 19 is a perspective view of the scalpel of the invention with the shield in the distal position.
Figure 20:
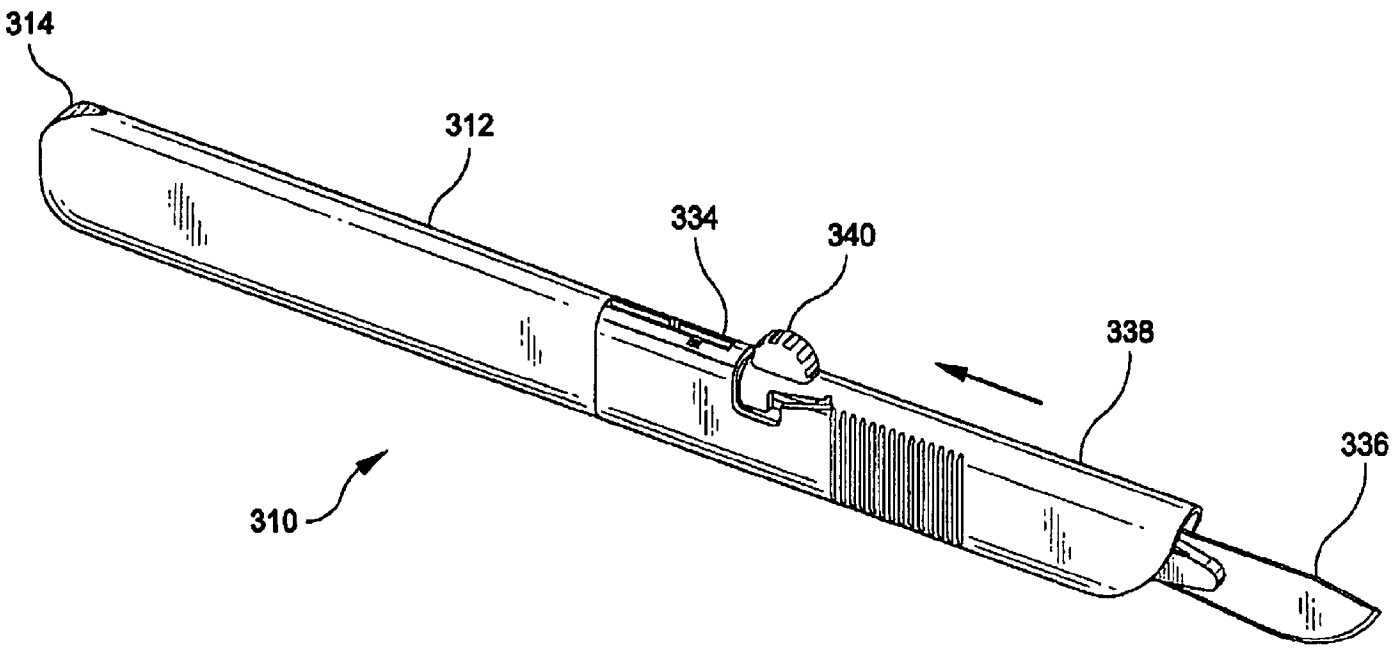
FIG. 20 is a perspective view of the scalpel of the invention with the shield in the proximal position.

Referring to FIGS. 16-24, a surgical scalpel 310 of the present invention includes an elongate handle 312 defining a longitudinal axis "A" has a proximal end 314 and a distal end 316. Scalpel 310 has a cartridge 318 removably mounted to handle 312 that includes a blade holder 320. Handle 312 has a first portion 322 having a first crosssectional area "X" with a first side 324 and an opposed second side 326, a second portion 328 having a larger crosssectional area "Y" than said first portion 322 and a third portion 329 having a larger cross-sectional area "Z" than second portion 328. Blade holder 320 has a proximal end 330 and a distal end 332. Referring to FIG. 18, proximal end 330 has an elongate cavity 334 therein for releasably receiving first portion 322 of handle 312 thereby removably mounting cartridge 318 to handle 312. Cartridge 318 includes a blade 336 that is fixedly attached to blade holder 320 so that when cartridge 318 is mounted to handle 312, blade 336 projects distally outwardly. Cartridge 318 further includes a shield 338 mounted on blade holder 320. Shield 338 is slidably movable between a distal position, best seen in FIG. 19, with shield 338 positioned to prevent substantially inadvertent access to blade 336 and a proximal position, best seen in FIG. 20, where shield 338 substantially surrounds second portion 328 and third portion 329 of handle 312 and blade 336 is exposed for use. Shield 338 has a releasable latch 340 for retaining shield 338 in the distal position and the proximal positions.

Figure 21:
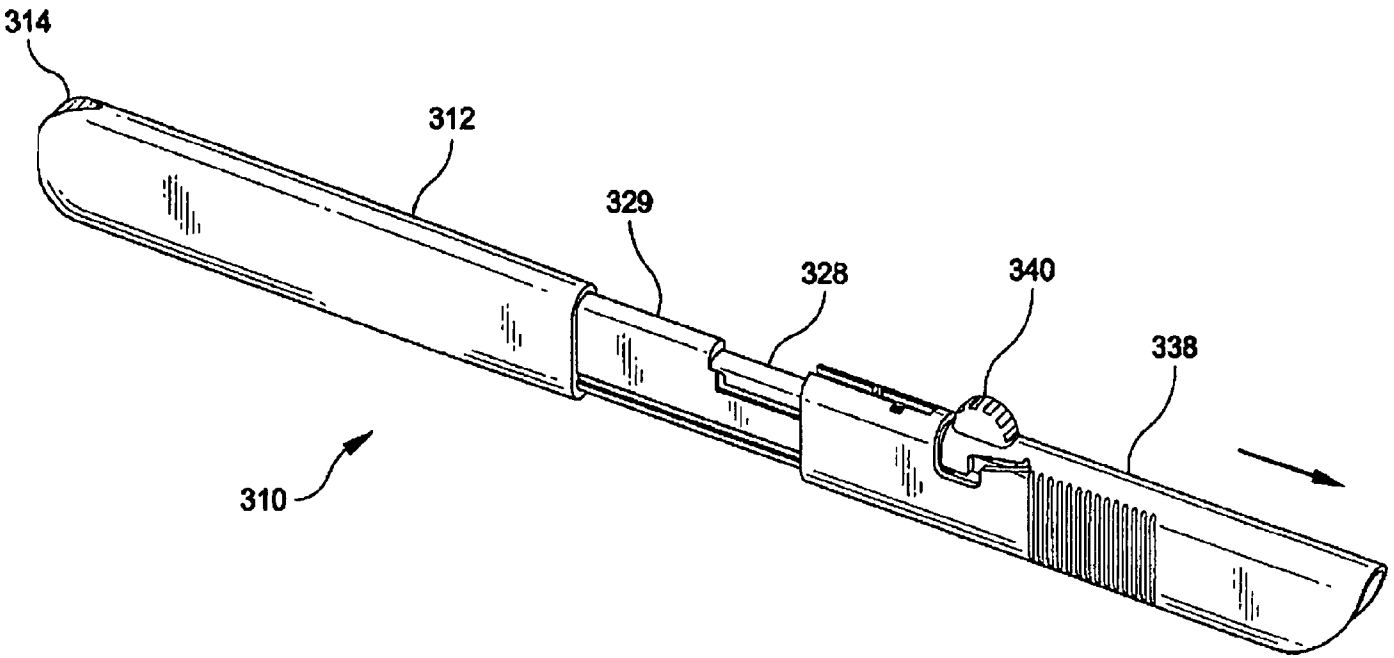
FIG. 21 is a perspective view of the scalpel of the invention with the cartridge partially removed from the handle.
Figure 22:
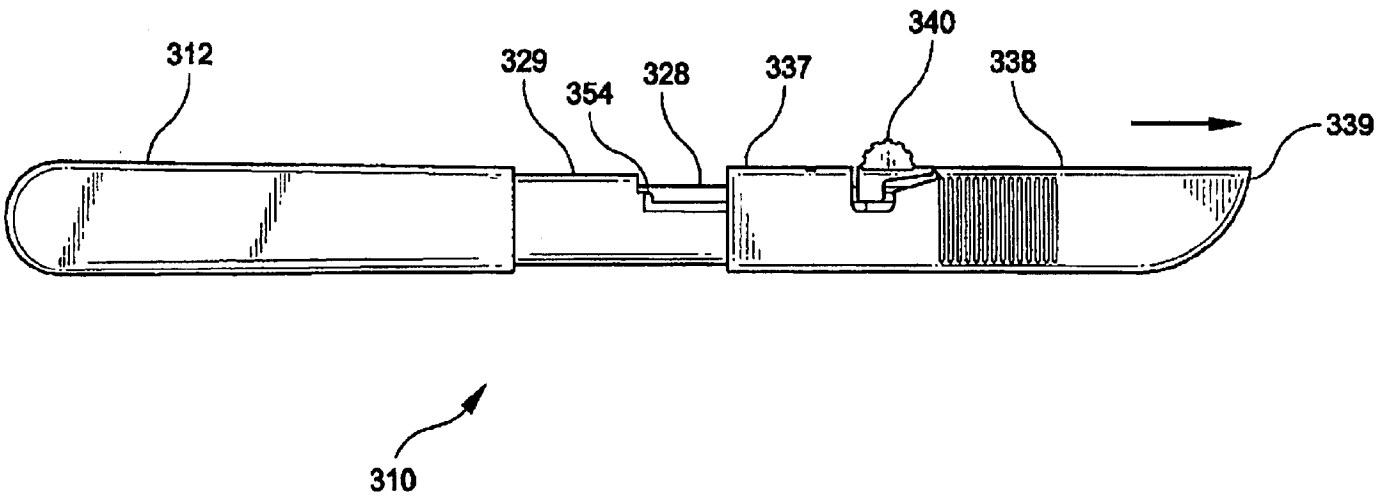
FIG. 22 is a side elevation of the scalpel of the invention analogous to FIG. 21 with the cartridge partially removed from the handle.
Figure 23:
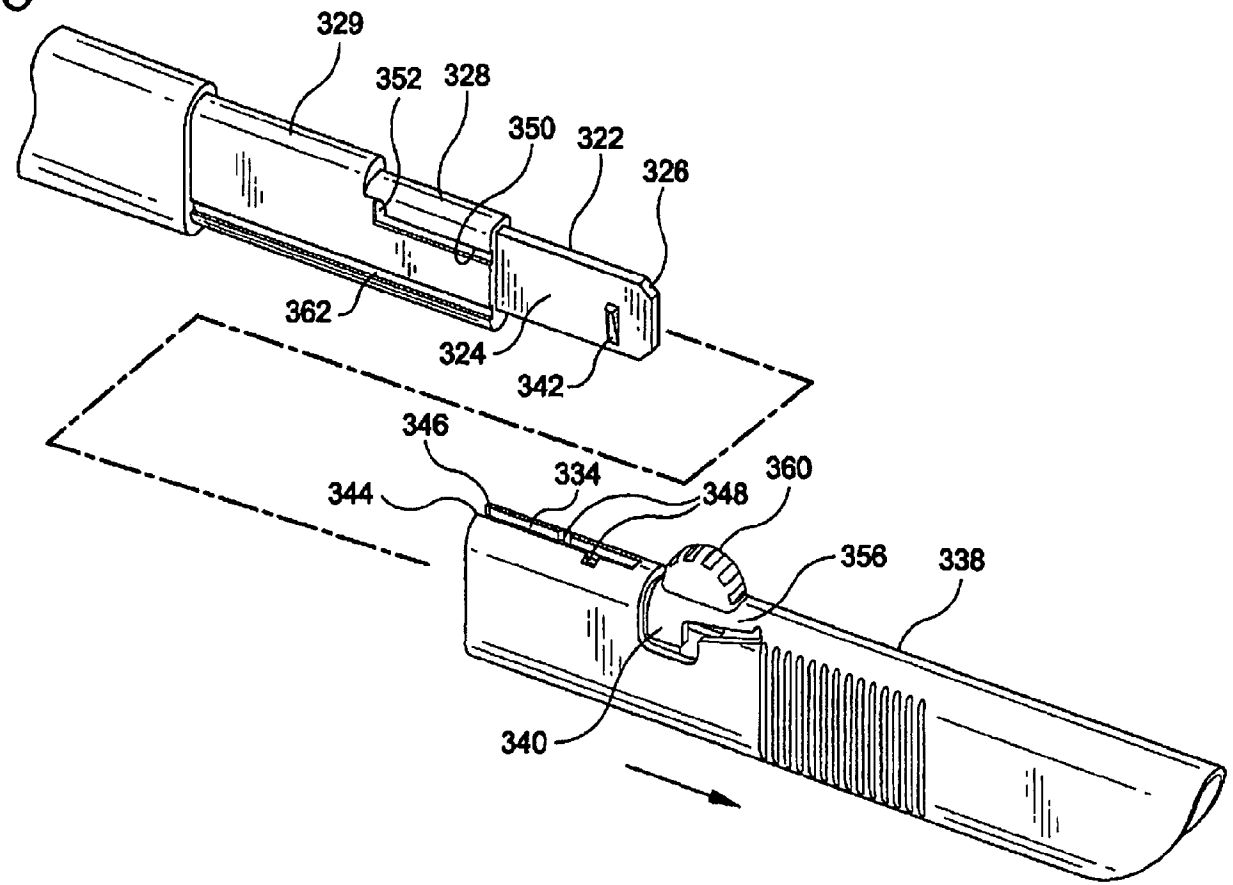
FIG. 23 is a partial exploded perspective view showing the removal of the cartridge from the handle; [and]

As shown in FIG. 18, first side 324 and said second side 326 of first portion 322 of handle 312 each include at least one outward projection 342 thereon. Cavity 334 further includes opposed sidewalls 344 and 346 with recesses 348 that are disposed to engage each of outward projections 342 on first portion 322 of the handle when handle 312 is received into cavity 334 in the blade holder from a direction generally orthogonal to longitudinal axis "A" and shield 338 is in the distal position. Referring now to FIGS. 21, 22 and 23, cartridge 318 is dismountable from handle 312 by disengagement of recesses 348 from projections 342 by removal of cartridge 318 from the handle in an axial distal direction by an outward deflection of sidewalls 344 and 346 of cavity 334 when shield 338 is in the distal position. When shield 338 is in the proximal position, sidewalls 344 and 346 are substantially precluded from outward deflection by the presence of shield 338, thus retaining the cartridge on the handle. Additionally, outward projections 342 are preferably disposed and shaped to facilitate the placement of cartridge 318 into cavity 334 from the direction orthogonal to the axis "A" and shaped to substantially resist the opposite orthogonal movement to axis "A" to remove the cartridge from the cavity. Thus, a force to remove cartridge 318 from cavity 334 in a direction orthogonal to axis "A" is greater than the force required to place the cartridge onto the handle.

Shield 338 is selectively retained in the proximal and distal positions by a latch that includes at least one, preferably two grooves 350, that extend from distal end 332 to said proximal end 330 of blade holder 320 on opposite sides of the blade holder. Grooves 350 continue into second portion 328 of handle 312. Grooves 350 each include a distal stop 352 in blade holder 320 and a proximal stop 354 in second portion 328. Shield 338 includes a cantilever 356 that has at least one, preferably two, inward projections 358 that are sized and positioned to fit within grooves 350 and engage distal stops 352 when shield 338 is in the distal position, and engage proximal stops 354 when shield 338 is in the proximal position. Cantilever 356 has a digit press surface 360 projecting upwardly, so that a practitioner's digital pressure sufficient to deflect cantilever 356 downwardly disengages projections 358 from one set of stops to allow the practitioner selectively to move shield 338 between the proximal position and the distal position. Referring to FIGS. 16 and 18, that show how first portion 322 is fit within cavity 334 to mount cartridge 318 to handle 312 and latch 340 that retains shield 338 in the proximal position until cantilever 356 is deflected, shield 338 is substantially unlikely to be moved to the proximal position inadvertently. Movement of shield from the proximal position requires both deflection of cantilever 356 to disengage projections 358 from the proximal stops 354 followed by proximal movement of the shield. When handle 312 is not present, even if cantilever 356 is deflected sufficiently to disengage projections 358 from proximal stops 354, there is nothing to push against to move the shield proximally with respect to blade holder 320 to move shield proximally and inadvertently expose blade 336.

Grooves 350 have a first depth "a" between distal end 332 of blade holder 320 and distal stops 352 and a second depth "b" between distal stops 352 and proximal stops 354, second depth "b" being deeper than first depth "a" so that as cartridge 318 is assembled by placement of a proximal end 337 of shield 338 onto blade holder 320 distal end 332 with inward projections 358 positioned in grooves 350, a proximal axial movement of shield 338 outwardly deflects inward projections 358 until the projections reach distal stop 352 whereupon projections 358 reach second depth "b" and are no longer deflected thereby serving to retain shield 338 on blade holder 320. When cartridge 318 is not mounted to handle 312, deflection of cantilever 356 can only disengage projections 358 from distal stops 354, movement of the projections back into the portion of grooves 350 with depth "a" would require use of some sort of a tool, thus substantially preventing inadvertent distal movement of the shield, removal of the shield from the blade holder and inadvertent exposure of the blade.

Blade holder 320 further includes at least one, preferably two, channels 362 extending from distal end 332 of blade holder 320 to second portion 328 of handle 312 when cartridge 318 is mounted on handle 312. Shield 338 includes at least one, preferably two rails 364 sized and positioned to cooperatively slide within channels 362 thereby to facilitate movement of shield 338 between the proximal and the distal positions.

Figure 24:
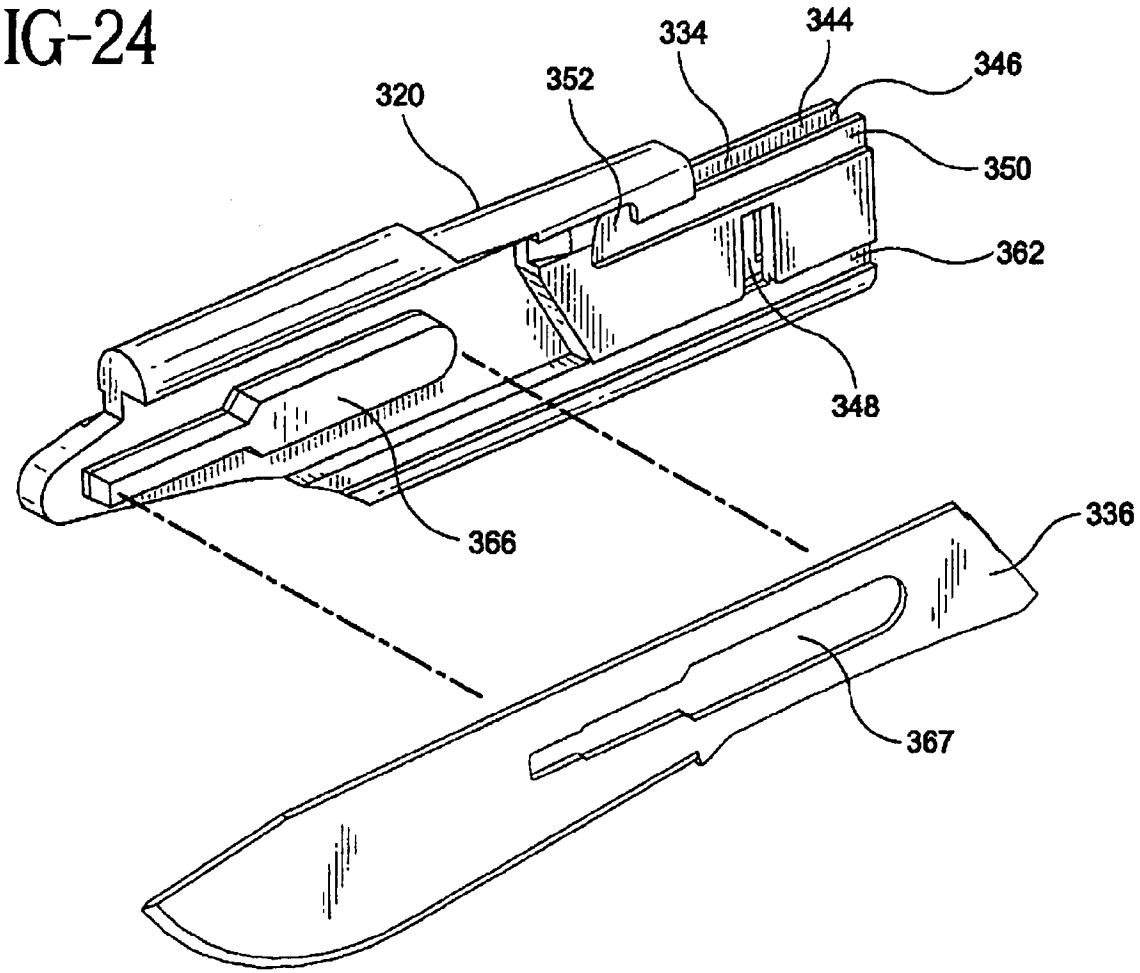
FIG. 24 is a perspective view of the blade holder of the invention[.]*;*

Referring to FIG. 24, blade holder 320 includes an outward projection 366 sized and shaped to fit an aperture 367 in blade 336 for mounting blade 336 to the blade holder. Blade 336 may be fixedly attached to the blade holder 320 by heat staking, adhesive bonding or any other type of attachment known to be satisfactory for forming such an attachment. It is the intention of the invention that blade 336 not be removable from the blade holder without rendering the blade holder substantially non-functional. Preferably, blade 336 is fixedly attached to blade holder 320 by a heat staking process to provide the fixed and substantially rigid attachment of the blade that is required by practitioners. Blade 336 may be any size or shape blade commonly used for surgical procedures and formed from any materials commonly used for such blades. Preferably, blade 336 is formed from a stainless steel and sharpened to a fine cutting edge.

Blade holder 320 may be formed from thermoplastic materials such as polypropylene, polyethylene, polycarbonate, polysulfone, polyacetal, polyamide and the like. Shield 338 may be formed from thermoplastic materials such as polypropylene, polyethylene, polycarbonate, polyacetal, and polyamide and the like. For particular applications shield 338 may be formed from a substantially transparent material. Handle 312 may be formed from a material such as machined metal, formed powdered metal and thermoplastic or thermoset materials. In the preferred application, shield 338 and blade holder 320 are formed from thermoplastic materials such as polypropylene and polycarbonate with a stainless steel blade to form the single-use cartridge 318. [flandle] *Handle* 312 preferably is formed from machined metal or formed powdered metal to provide a durable reusable device that provides the practitioners with the same "feel" and "heft" that they are accustomed to with the current reusable handles and with removable single-use bare blades. Handle 312 preferably has a surface treatment, here illustrated as knurling 313, to improve the practitioner's ability to securely grip the scalpel. Other surface treatments including roughening, grooving, checkering and the like may be preferred for particular applications and are considered within the scope of the invention.

Preferably, cartridge 318, with shield 338 in the distal position where blade 336 is protected, is placed in a package 370, indicated in phantom in FIG. 17, formed from materials substantially resistant to the passage of microorganisms and package 370 is sealed. Preferably, sealed package 370 is then exposed to conditions that would render any microorganisms inside the package substantially non-viable. Packaged cartridges then may be considered "sterile" until the package is opened to arm the reusable handle. Preferably, the handles are subjected to a cleaning and sterilization process by the practitioner prior to their presentation for the cartridge loading. Suitable materials for forming package 370 include, but are not limited to, paper, nonwoven materials such as spunbonded polyolefin and the like, polymeric films, metallic foils and composites of these materials. Suitable techniques for rendering microorganisms within package 370 non-viable include, but are not limited to, exposure to chemical agents such as ethylene oxide, gaseous hydrogen peroxide and the like, ionizing radiation, such as gamma radiation from $Co^{60}$, electron beam radiation, dry heat and steam sterilization. When selecting materials for forming scalpel 310 and package 370, consideration of the particular materials' tolerance for the sterilization method should be made.

A method for using scalpel 310 includes opening package 370 to expose a proximal end 319 of cartridge 318. Handle 312 is then fitted to the cartridge and removed from the package. Depending upon the choice of the individual practitioner or the institution use protocol, scalpel 310 may be passed to the practitioner with shield 338 in the distal position as it is removed from package 370. Upon receiving scalpel 310, the practitioner applies digital pressure to press surface 360 to disengage projections 358 from distal stops 352 and withdraw shield 338 to the proximal position to expose blade 336 for the desired procedure. After the practitioner has completed the procedure, the practitioner applies digital pressure to press surface 360 to disengage projections 358 from proximal stops 354 and return shield 338 to the distal position to pass scalpel 310 to the support person with blade 336 protected from inadvertent exposure. With shield 338 in the distal position, the support personnel may then remove cartridge 318 from handle 312 and dispose of it according to the institution protocol. Handle 312 may then be subject to cleaning and sterilization according to the institution protocol and returned for further use.

An alternative for particular applications, is to form handle 312 from similar materials as blade holder 320, mount cartridge 318 to handle 312, complete the desired procedure, and then dispose of entire scalpel 310 after the procedure is completed.

Referring now to FIGS. 25-36C, a more preferred embodiment of the scalpel 410 of the invention includes an elongate handle 412 defining a longitudinal axis "A" that has a proximal end 414 and a distal end 416. Scalpel 410 further includes a cartridge 418 that is removably mounted to handle 412. Cartridge 418 has a blade holder 420 with a proximal end 422 and a distal end 424 with a blade 426 fixedly attached that is disposed so that blade 426 projects distally outwardly when cartridge 418 is mounted to handle 412. Cartridge 418 also includes a shield 430 that is releasably slidably mounted onto blade holder 420 for movement between a distal position, best seen in FIG. 28, where shield 430 substantially prevents inadvertent access to blade 426 and a proximal position, best seen in FIG. 29, where shield 430 substantially surrounds a portion of handle 412 and blade 426 is exposed for use. Cartridge 418 is releasably mountable to handle 412. Additionally, shield 430 is substantially not moveable with respect to blade holder 420 unless cartridge 418 is mounted on handle 412.

Shield 430 includes a cantilever 432 with a digital activation section 434 projecting upwardly from a top surface 435 of the shield. When cartridge 418 is mounted on handle 412, a practitioner may apply digital pressure to digital activation section 434 sufficient to downwardly deflect cantilever 432 and release shield 430 for movement between the proximal position and the distal position. Scalpel 410 has a groove 436 that extends from the blade holder 420 from a distal terminus 438 onto handle 412 to a proximal terminus 440 on one side of the scalpel. Preferably, scalpel 410 has a groove 436 on each of a first side 437 and a second side 439, each with distal termina 438 on blade holder 420 and proximal termina 440 on handle 412. Cantilever 432 further includes at least one boss 442, preferably two bosses 442 disposed to engage each of grooves 436. Each termina of groove 436 is an upward enlargement disposed to engage bosses 442 when shield 430 is positioned in either the proximal or distal positions. When bosses 442 are engaged in the termina, shield 430 is substantially prevented from movement. When the practitioner applies sufficient downward force to digital application section 434 to deflect cantilever 432, bosses 442 are no longer engaged with the upward enlargements at the terminal thereby allowing the practitioner to selectively move shield 430 between the proximal and distal positions as desired. Bosses 442 track in grooves 436 to stabilize shield 430 during the movement between positions, and when a terminus is reached, bosses 442 preferably serve to provide a practitioner perceptible "snap" as the bosses engage the enlargement and allow cantilever 432 to return to the rest position to assist the practitioner in recognition of the completion of desired movement of the shield.

Figure 27:
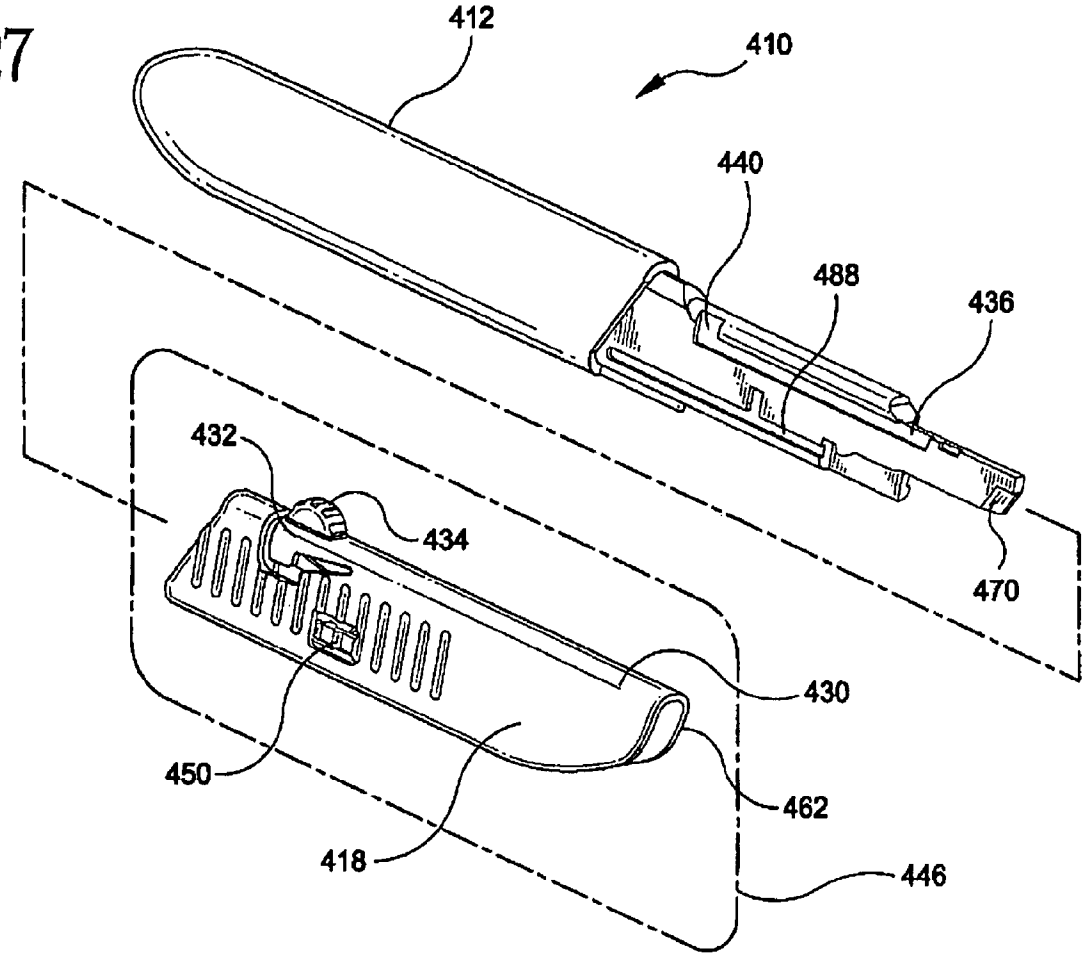
FIG. 27 is a perspective view of the scalpel of FIG. 25 prior to assembly.

Cartridge 418 is preferably supplied sealed in a package 446, illustrated in phantom in FIG. 27, formed from materials substantially resistant to the passage of microorganisms and exposed to conditions that render any microorganisms within package 446 substantially non-viable. Suitable materials for forming package 446 include. but are not limited to, paper, polymeric films, non-wovens, metallic foils, and combinations of these materials. Suitable conditions for rendering microorganisms non-viable include, but are not limited to, chemical agents such as ethylene oxide and gaseous hydrogen peroxide, ionizing radiation such as gamma, electron beam, ultra-violet and the like.

Cartridge 418 is supplied separately and includes blade 426, which is preferably formed from a material such as stainless steel. carbon steel or a ceramic that is suitable for being formed to a sharpened edge for cutting. Shield 430 is substantially not movable with respect to blade holder 420 unless cartridge 418 is properly fully mounted on handle 412 and the practitioner handling the scalpel is intentionally moving the shield. Practitioners and service personnel are thus substantially protected from inadvertent exposure to the blade during assembly of the cartridge to the handle, during handling to prepare for or after a procedure, or during clean-up and disposal of a cartridge after removal from the handle.

Figure 25:
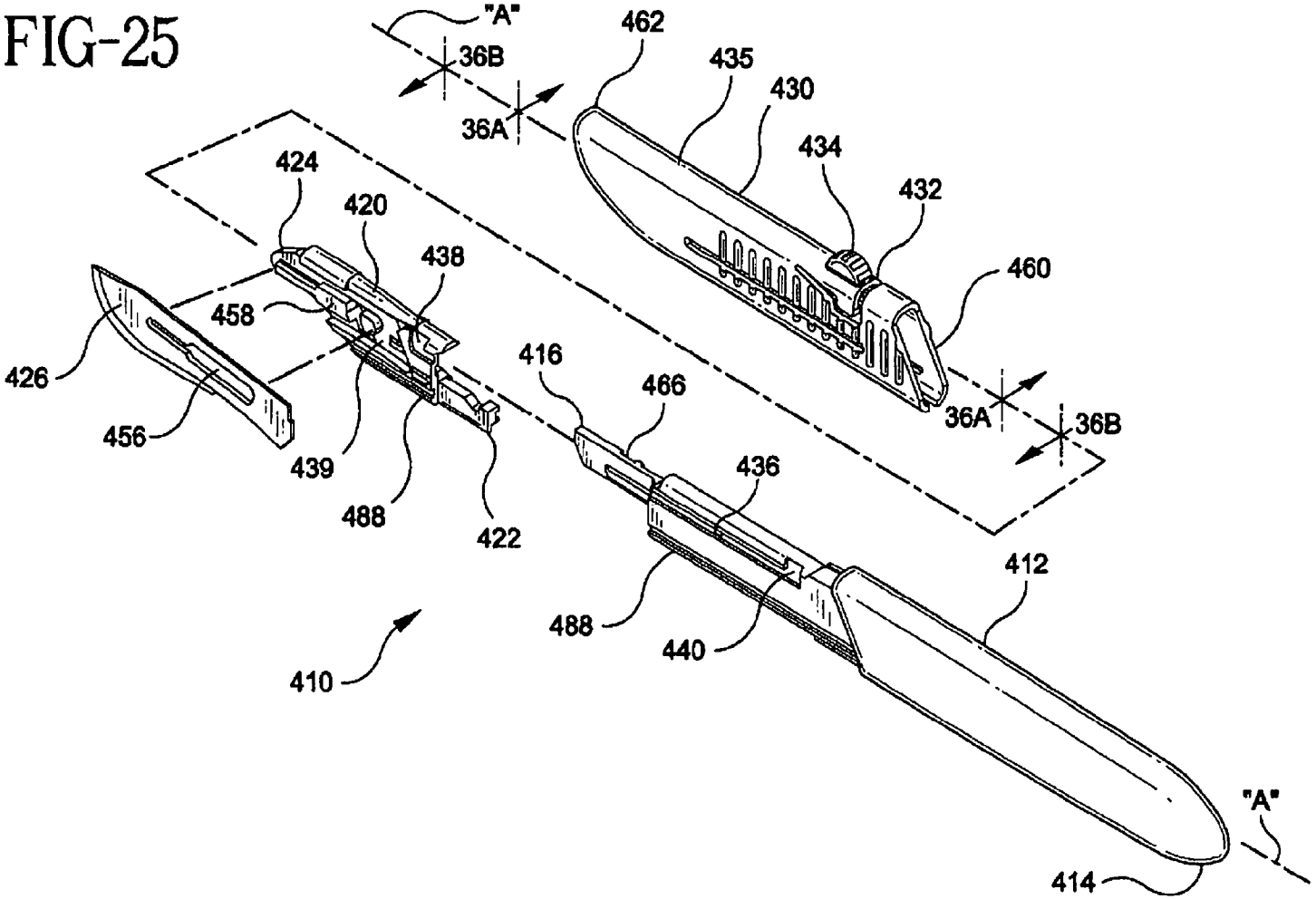
FIG. 25 is an exploded perspective view of a preferred embodiment of the scalpel of the invention.
Figure 26:
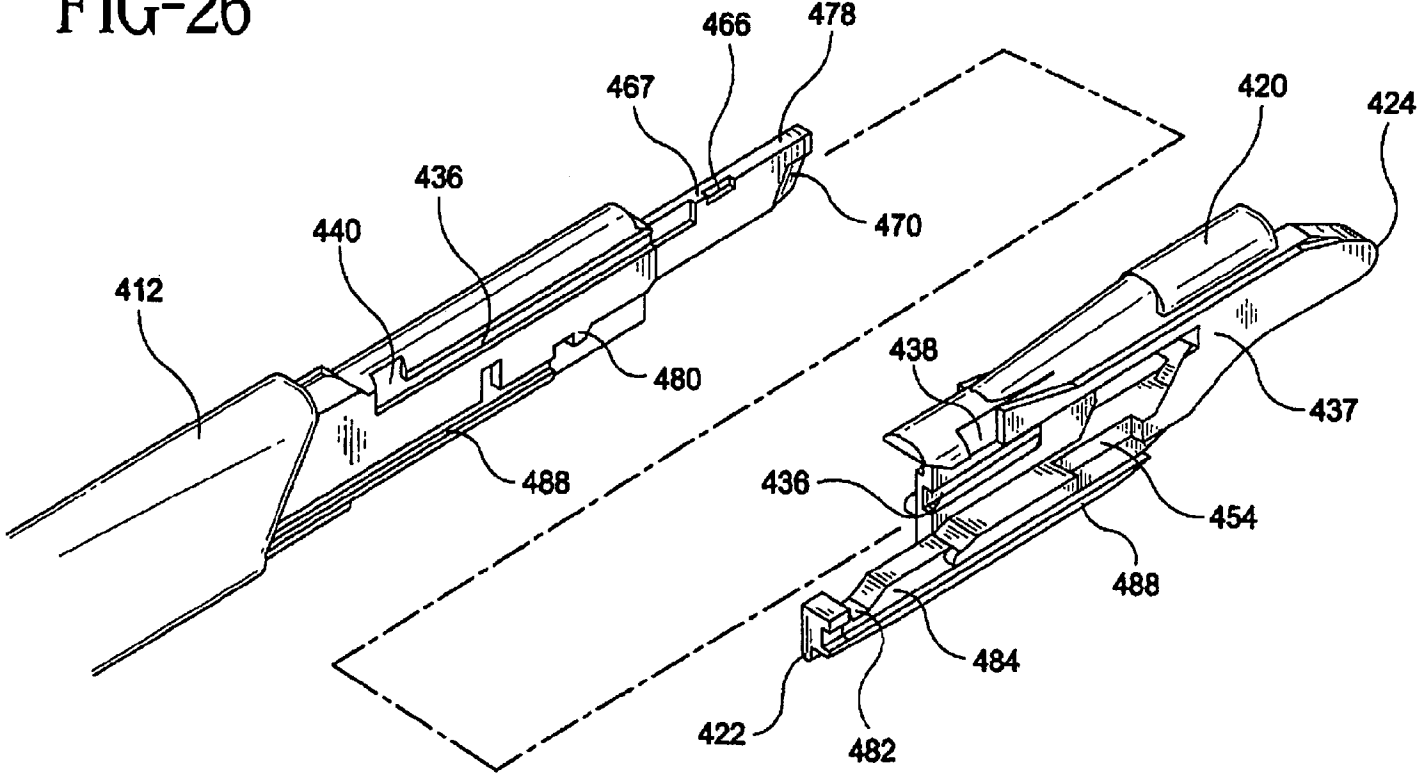
FIG. 26 is an exploded perspective view of a portion of the scalpel of FIG. 25.
Figure 33:
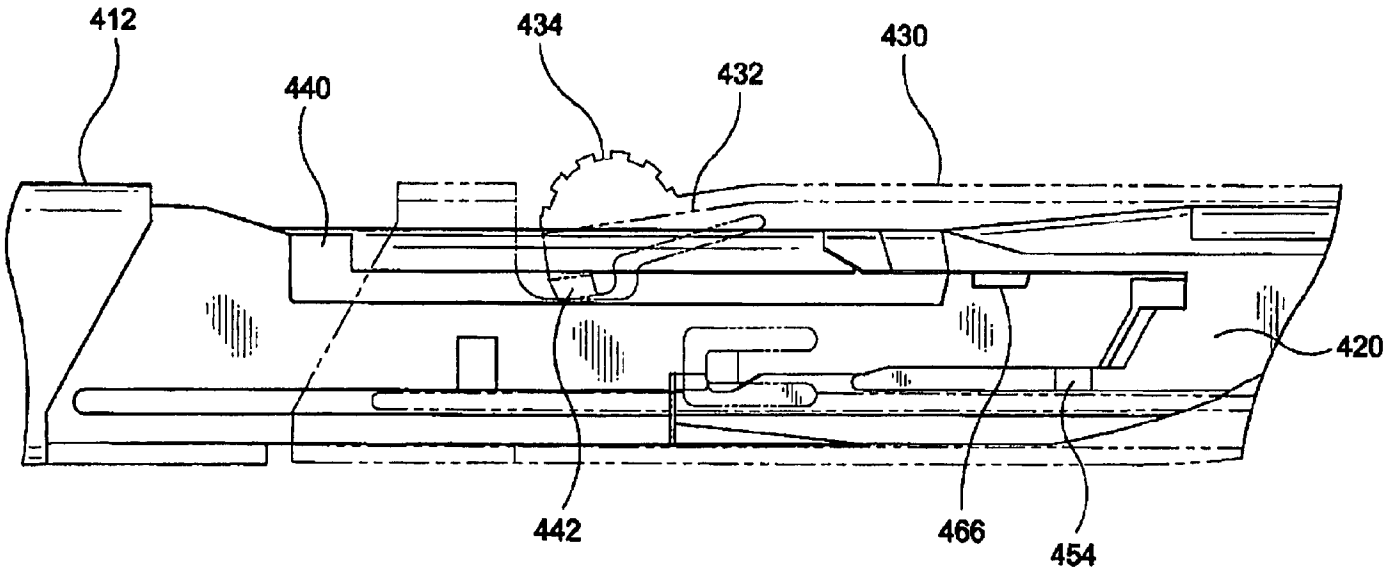
FIG. 33 is a schematic side elevation view of a portion of the scalpel of FIG. 25.
Figure 34C:
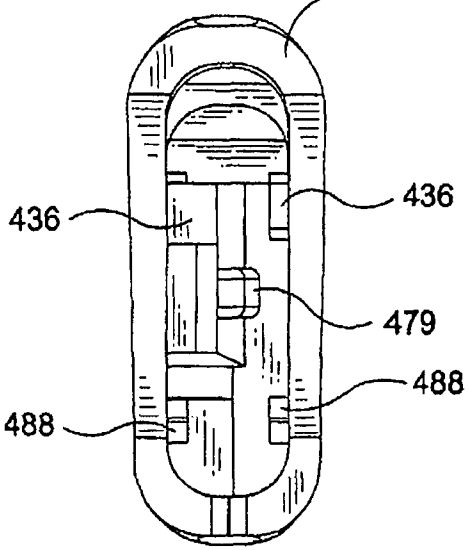
FIG. 34C is a distal end view of the handle of the scalpel of FIG. 25.
Figure 34A:
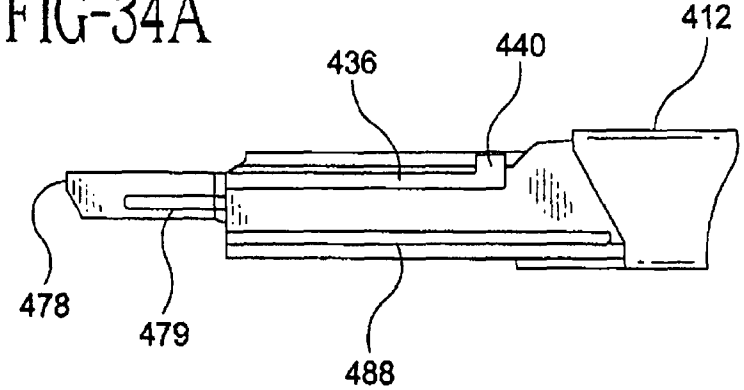
FIG. 34A is a side elevation view of a portion of one side of the distal portion of the handle of the scalpel of FIG. 25.
Figure 34B:
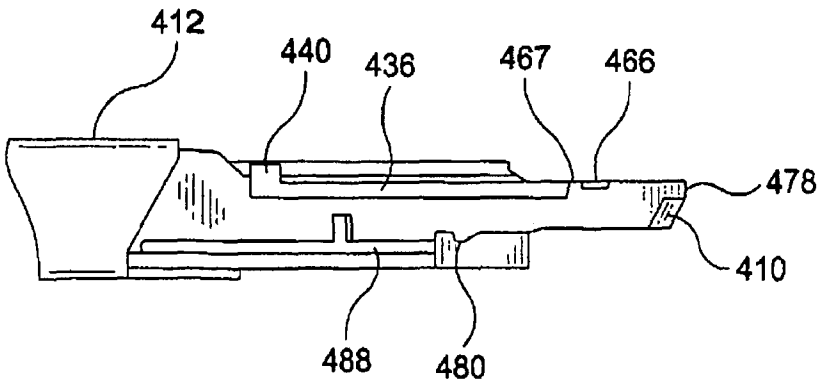
FIG. 34B is a side elevation view, analogous to FIG. 34A, of the other side of the distal portion of the handle of the scalpel of FIG. 25.
Figure 35C:
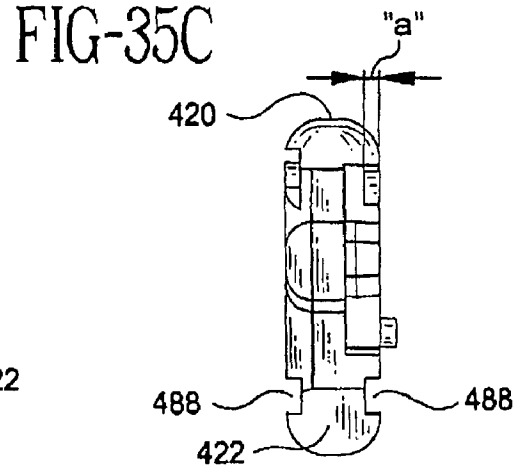
FIG. 35C is a distal end view of the blade holder of the scalpel of FIG. 25.
Figure 35D:
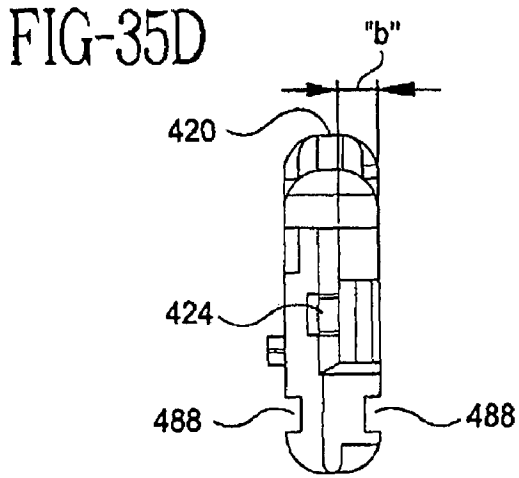
FIG. 35D is a proximal end view of the blade holder of the scalpel of FIG. 25.
Figure 35A:
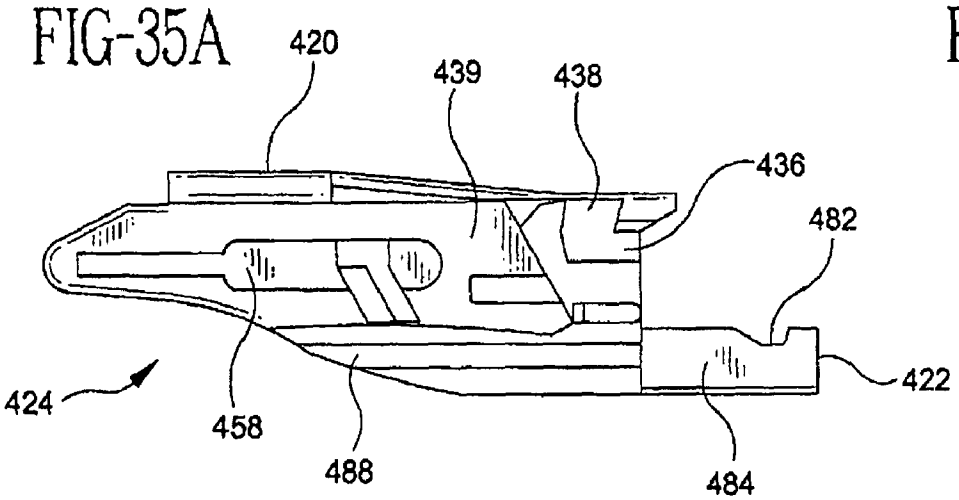
FIG. 35A is a side elevation view of one side of the blade holder of the scalpel of FIG. 25.
Figure 35B:
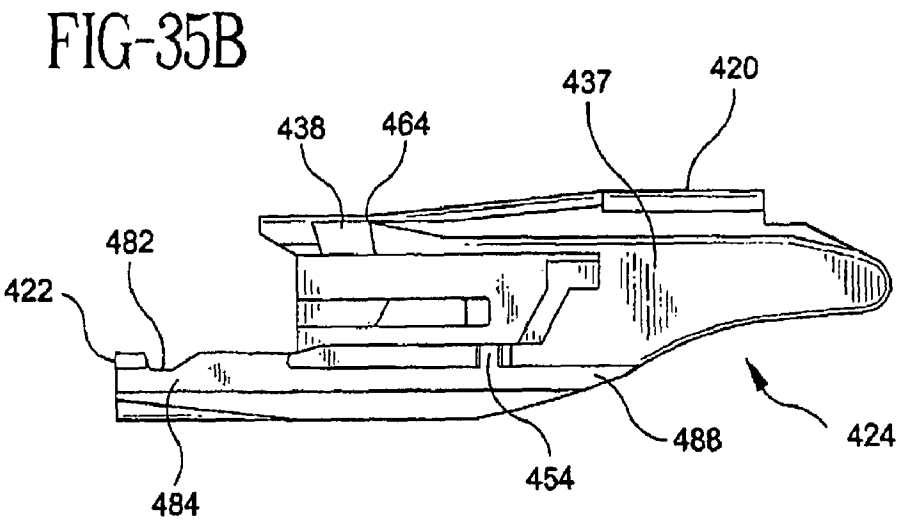
FIG. 35B is a side elevation view, analogous to FIG. 35A, of the other side of the blade holder of the scalpel of FIG. 25.
Figure 36C:
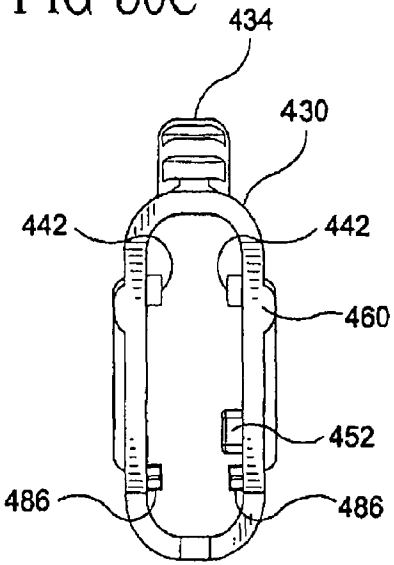
FIG. 36C is an end view of the proximal end of the shield of the scalpel of FIG. 25.
Figure 36A:
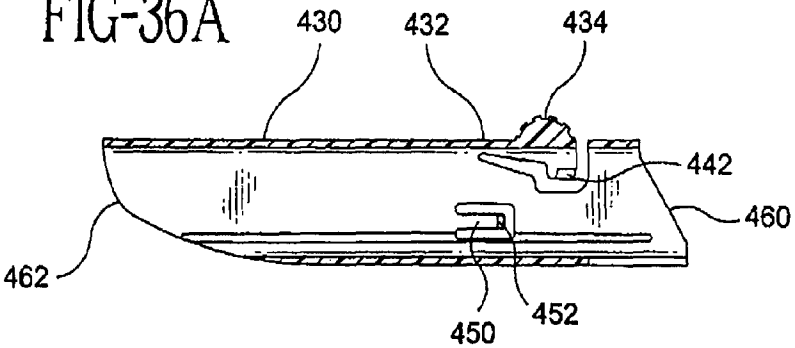
FIG. 36A is a cross-sectional view of the shield of the scalpel taken from FIG. 25 along the line 36A-36A.
Figure 36B:
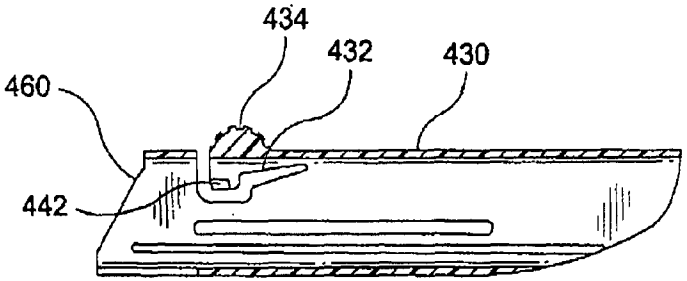
FIG. 36B is a cross-sectional view of the shield of the scalpel taken from FIG. 25 along the line 36B-36B.

Shield 430 preferably includes a deflectable tab 450, best seen in FIGS. 27, 28, 32 and 32A, with an inwardly projecting lug 452 that is disposed to engage a seat 454 in blade holder 420. Seat 454 is best seen in FIGS. 26, 33 and 35B. During initial assembly of cartridge 418, preferred blade 426 with an aperture 456 is fixedly attached to an outward protuberance 458 on blade holder 420 by fitting aperture 456 over protuberance 458 so that blade 426 is substantially rigid with respect to blade holder 420. Suitable fixed attachments of blade 426 to blade holder 420 are formed by heat staking the projection onto the aperture, adhesive bonding or the like. Shield 430 has a proximal end 460 and a distal end 462. The assembly then includes substantially axially aligning proximal end 460 of the shield with distal end 424 of the blade holder and proximally advancing the shield onto the blade holder to form cartridge as shown in FIG. 25. As is best seen in FIGS. 35A, 35B, 35C and 35D grooves 436 have a first depth "a" between distal termina 438 on the blade holder *and a shoulder 464* and a second depth "b" between [distal termina 438] *the shoulder 464* and distal end 424 of the blade holder. Second depth "b" is less than first depth "a" thereby to form a shoulder 464 at the intersection of depths "a" and "b". As shield 430 is proximally advanced onto blade holder 420, bosses 442 engage grooves 436 at second depth "b" and deflect. As shield 430 is further proximally advanced onto the blade holder, bosses 442 engage deeper first depth "a" at distal termina 438 and are substantially prevented from returning to second depth "b" region by shoulder 464 thereby substantially preventing distal movement of shield 430 with respect to blade holder 420. Tab 450 with inwardly projecting lug 452 is disposed to engage seat 454 in blade holder 420 when bosses 442 are in distal termina 438, thus substantially preventing further movement of shield 430 with respect to blade holder 420 until cartridge 418 is mounted onto handle 412.

Preferably, shield 430 is substantially prevented from movement with respect to blade holder 420 during mounting of cartridge 418 onto handle 412 even if the practitioner unintentionally applies sufficient pressure to digital activation surface 434 to deflect cantilever 432. [Proximal end 414]

*Distal end 416* of handle 412 is preferably disposed to engage at least one of bosses 442 as cartridge 418 is proximally advanced onto handle 412 when cantilever 432 is deflected downwardly. Additionally if the practitioner were to inadvertently apply pressure to digit activation surface 434 after cartridge 418 is partially properly advanced onto handle 412, preferred handle 412 further includes a recess 466 disposed on a top surface 467 of handle 412 to engage at least one of bosses 442 to function as a false stop and substantially prevent further advancement of cartridge 418 onto handle 412.

As cartridge 418 is fully seated on handle 412, a distal prong 478 on handle 412 with a chamfered surface 470 is preferably disposed to engage tab 450 and disengage inwardly projecting lug 452 from seat 454 on blade holder 420, thus allowing movement of shield 430 with respect to blade holder 420 when the practitioner intentionally applies sufficient pressure to digital activation surface 434 to downwardly deflect cantilever 432. Preferably, distal prong 478 is stiffened by a rib 479 on one side.

Figure 28:
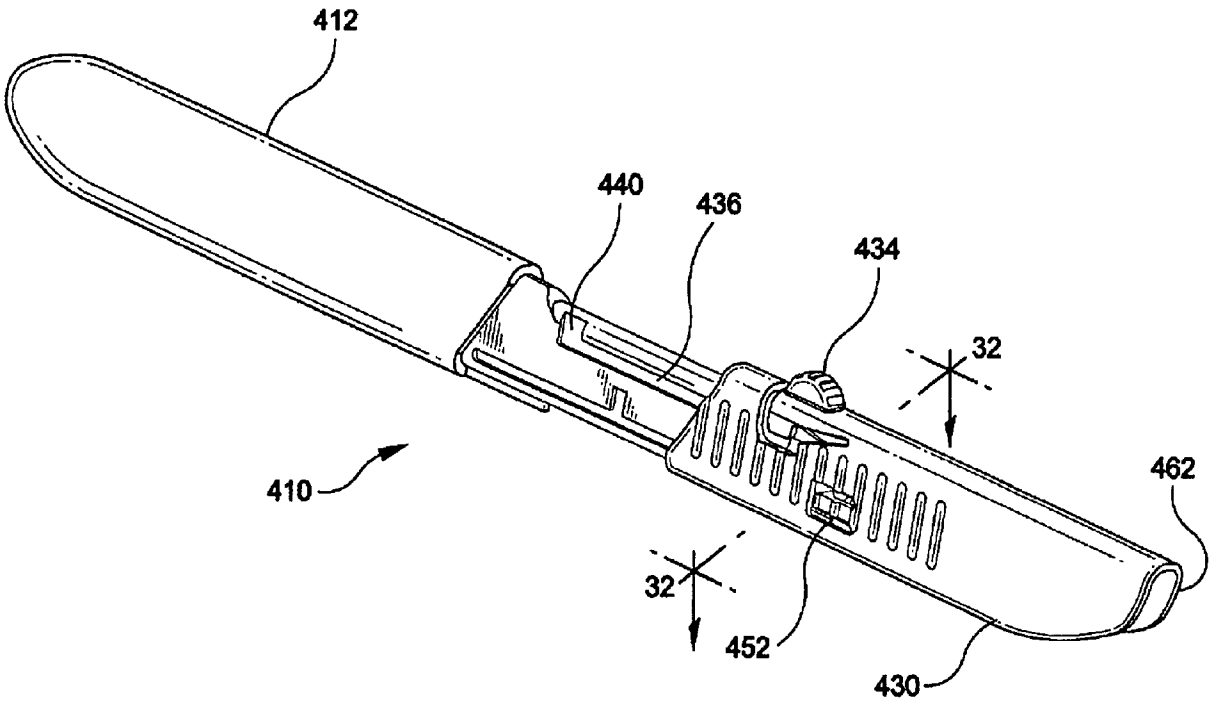
FIG. 28 is a perspective view of the scalpel of FIG. 25 as assembled with the shield substantially preventing inadvertent exposure to the blade.
Figure 29:
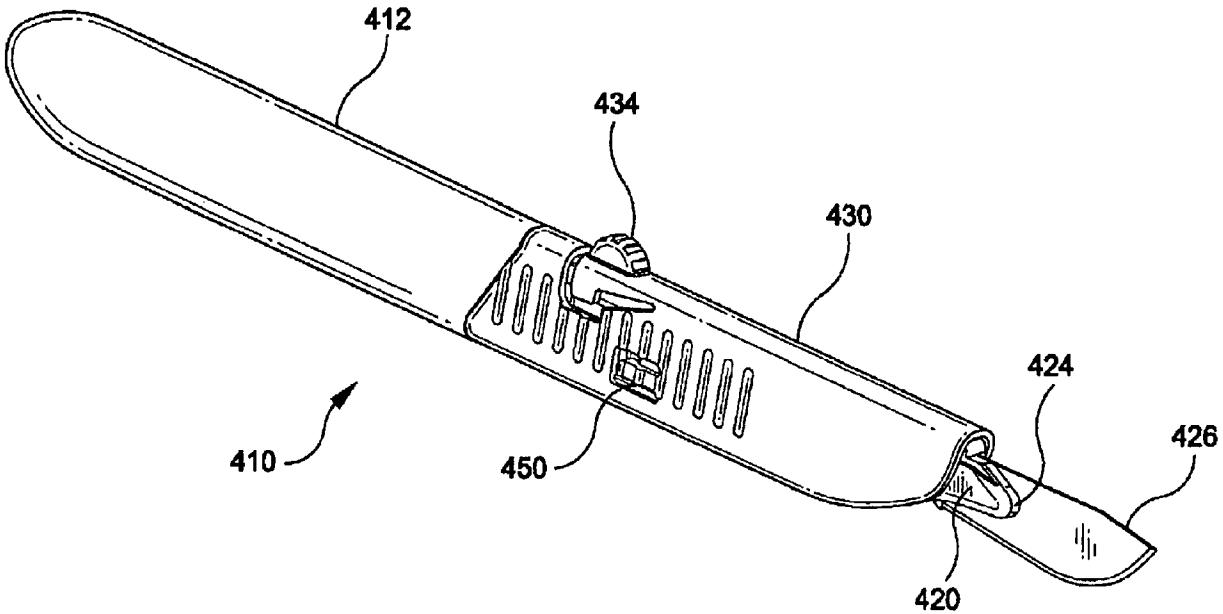
FIG. 29 is a perspective view of the scalpel of FIG. 25, analogous to FIG. 28, with the blade exposed for use.
Figure 30:
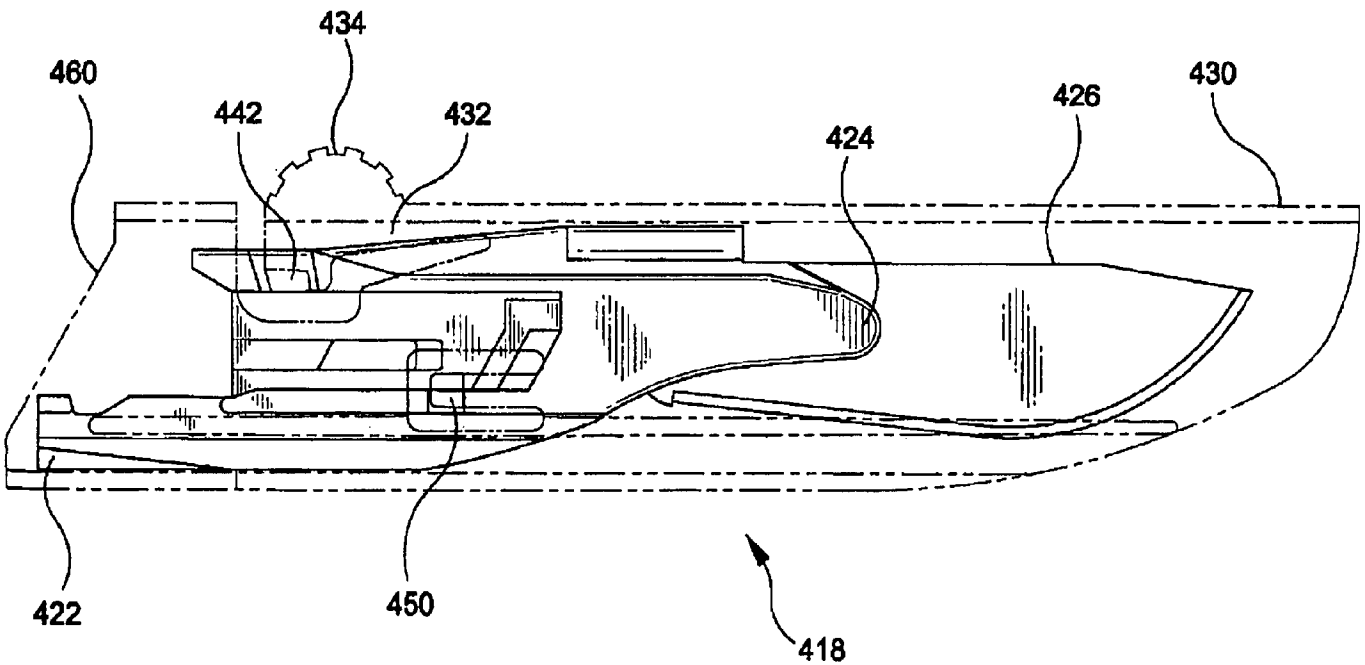
FIG. 30 is a schematic side elevation view of a portion of the scalpel of FIG. 25.
Figure 31:
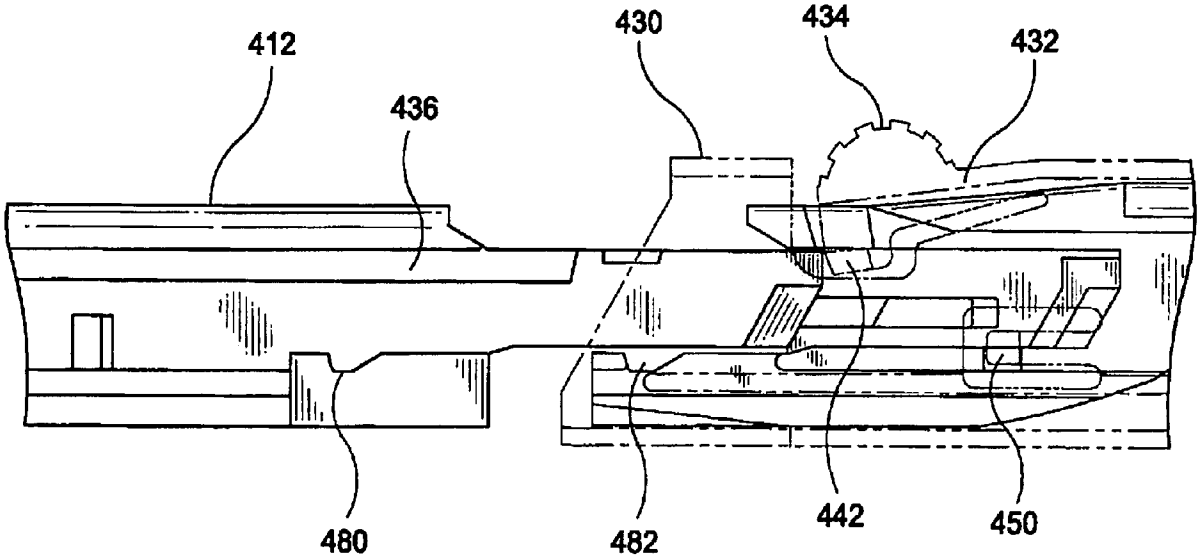
FIG. 31 is a schematic side elevation view of another portion of the scalpel of FIG. 25.
Figure 32:
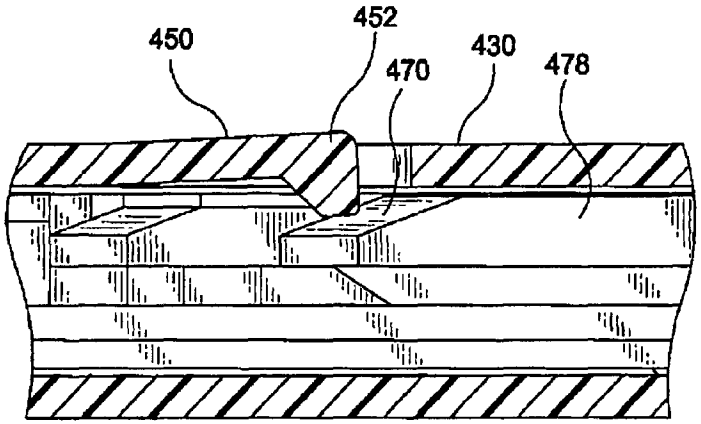
FIG. 32 is a schematic partial horizontal cross section view of the scalpel of FIG. 25 taken from FIG. 28 along the line 32-32.
Figure 32A:
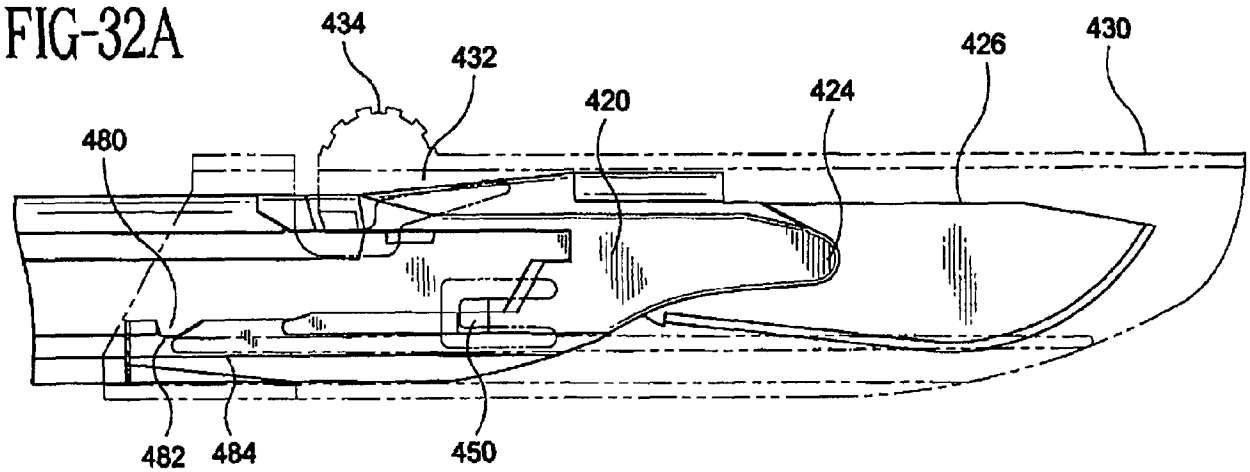
FIG. 32A is a schematic side elevation view of a portion of the scalpel of FIG. 25.

Cartridge 418 is releasably mounted to handle 412 by engaging a downward projection 480 on handle 412 with a pocket 482 on a flexible beam portion 484 that projects proximally from blade holder 420, best seen in FIGS. 25, 26, 30, 31 and 32A. To remove cartridge 418 from handle 412, cartridge 418 is distally advanced from handle 412. Preferably, shield 430 substantially surrounds blade holder 420 and substantially prevents inadvertent access to blade 426 when shield 430 is in the distal position, as best seen in FIG. 28. When shield 430 is proximal position, as best seen in FIG. 29, blade 426 is exposed for use, bosses 442 are disposed in proximal termina 440 and shield 430 surrounds at least a portion of handle 412. Since shield 430 substantially surrounds at least a portion of the handle when is in the proximal position, beam 484 is substantially prevented from flexing downwardly to release projection 480 from pocket 482 by the shield, thus substantially preventing cartridge 418 from being dismounted from handle 412 when the blade is exposed. Additionally, if a practitioner inadvertently applies distal force to attempt to move the shield to the distal position, the presence of bosses 442 in proximal termina 440 substantially prevent movement of shield 430 to the distal position. To move shield 430 to the distal position, the practitioner must apply sufficient force to the digital activation surface 434 to downwardly deflect cantilever 432 and release bosses 442 from the proximal termina 440. If a practitioner grasps shield 430 and attempts to remove cartridge 418 from handle 412 after shield 430 is released from the proximal position, but before shield 430 is fully seated in the distal position and blade 426 is substantially protected from inadvertent access, shield 430 substantially prevents the disengagement of pocket 482 from projection 480 until the shield is distally advanced to substantially protect blade 426 from inadvertent access. Then, as handle 412 is separated from cartridge 418, prong 478 is disengaged from tab 450 thereby allowing lug 452 to engage seat 454 and substantially prevent movement of shield 430 with respect to blade holder 420.

Preferably, shield 430 includes inwardly projecting rails 486 disposed to slidably engage conjugate slots 488 on both sides of blade holder 420 and handle 412 to provide stability to shield 430 during movement between the proximal and distal positions and to improve the overall rigidity and feel of scalpel 410 in the practitioner's hand.

Blade holder 420 may be formed from materials such as polymeric resins or metallic materials. Preferably, blade holder 420 is formed from thermoplastic materials such as polypropylene, polyethylene, polycarbonate, polysulfone, polyacetal, polyamide and the like. Shield 430 may be formed from thermoplastic materials such as polypropylene, polyethylene, polycarbonate, polyacetal, polyamide and the like. For particular applications, the material selected to form shield 430 may be substantially transparent. Handle 412 may be formed from thermoplastic materials such as polyethylene, polycarbonate, polysulfone, polypropylene, polyacetal, polyamide and the like. Preferably, handle 412 is formed from a metallic material such as formed powdered metal or machined metal. Preferably materials are selected to provide a substantially rigid structure for scalpel 410 that are compatible with most sterilization methods and provide practitioners with a scalpel that has similar "feel" and "balance" to current reusable devices or reusable handle devices intended to mount and dismount bare single-use blades.

In normal use, practitioners would receive cartridge 418 sealed in package 446. A method for assembling scalpel 410 includes opening package 446 to expose cartridge 418, and positioning the cartridge so that proximal end 422 of the blade holder is in substantial axial alignment with the distal end of handle 412. The practitioner then advances the cartridge proximally onto the handle until it is fully seated. At this point, the practitioner may apply finger pressure to the digital activation surface to downwardly deflect the cantilever and release the shield for movement from the distal position to the proximal position to expose the blade for use. After the use of the blade is complete, the practitioner releases the shield from the proximal position with finger pressure and moves shield 430 to the distal position. The practitioner then grasps the shield, applies distal force and removes the cartridge from the handle for disposal according to the institution's disposal protocol.

The scalpel of the invention provides practitioners with a scalpel that has the "feel" and "heft" of traditional reusable scalpels while additionally providing both practitioners and support personnel with a shielded blade that is unlikely to be inadvertently exposed. The removable cartridge allows the use of a sterile sharp blade for the procedure and substantially allows the blade to be protected from inadvertent exposure both during preparation for the procedure and after the procedure.

Referring now to FIGS. 37-40d, a further preferred embodiment of the scalpel of the invention is shown. In this embodiment, elements of the invention are substantially similar to those of the embodiment shown in FIGS. 25-36c. Accordingly, substantially similar elements that perform substantially similar functions are assigned similar reference characters of the "5" hundred series. Scalpel 510 of the invention includes an elongate handle 512 defining a longitudinal axis "A" that has a proximal end 514 and a distal end 516. Scalpel 510 further includes a cartridge 518 that is removably mounted to handle 512. Cartridge 518 has a blade holder 520 with a proximal end 522 and a distal end 524 with a blade 526 fixedly attached that is disposed so that blade 526 projects distally outwardly when cartridge 518 is mounted to handle 512. Cartridge 518 also includes a shield 530 with a proximal end 560 and a distal end 562 that is releasably slidably mounted onto blade holder 520 for movement between a distal position, similar to that shown for the previous embodiment shown in FIG. 28, where shield 530 substantially prevents inadvertent access to blade 526 and a proximal position, similar to that shown for the previous embodiment in FIG. 29, where shield 530 substantially surrounds a portion of handle 512 and blade 526 is exposed for use. Cartridge 518 is releasably mountable to handle 512. Additionally, shield 530 is substantially not moveable with respect to blade holder 520 unless cartridge 518 is mounted on handle 512.

Shield 530 includes a first cantilever 532 with a digital activation section 534 projecting upwardly from a top surface 535 of the shield. When cartridge 518 is mounted on handle 512, a practitioner may apply digital pressure to digital activation section 534 sufficient to downwardly deflect cantilever 532 and release shield 530 for movement between the proximal position and the distal position. Scalpel 510 has a groove 536 that extends from the blade holder 520 from a distal terminus 538 onto handle 512 to a proximal terminus 540 on one side of the scalpel. Preferably, scalpel 510 has a groove 536 on each of a first side 537 and a second side 539, each with distal termina 538 on blade holder 520 and proximal termina 540 on handle 512. Cantilever 532 further includes at least one boss 542, preferably two bosses 542, best seen in FIG. 39, disposed to engage each of grooves 536. Each termina of groove 536 is preferably an upward enlargement disposed to engage bosses 542 when shield 530 is positioned in either the proximal or distal positions. When bosses 542 are engaged in the termina, shield 530 is substantially prevented from movement. When the practitioner applies sufficient downward force to digital application section 534 to deflect cantilever 532, bosses 542 are no longer engaged with the upward enlargements at the termina, thereby allowing the practitioner to selectively move shield 530 between the proximal and distal positions as desired. Bosses 542 track in grooves 536 to stabilize shield 530 during the movement between positions, and when a terminus is reached, bosses 542 preferably serve to provide a practitioner perceptible "snap" as the bosses engage the enlargement and allow cantilever 432 to return to the rest position to assist the practitioner in recognition of the completion of desired movement of the shield. Preferably, termina 538 and 540 each include a roof portion 541 that substantially prevents boss 542 from upward disengagement from the termina. *Adjacent to roof portion 541 are ramped end portions 541b which define the ends of the cut away portion 541a. Roof portion 541 defines the bottom of the cut away portion 541a.*

Additionally, upward distal termina 538 has a distal surface 590 and a proximal surface 591, each with an upwardmost edge 593 and a lower edge 595. Preferably, the distance between the upwardmost edges 593 is greater than the distance between the lower edges, thereby causing a distal upward pitch to surface 590 and a proximal upward pitch to surface 591. The distal upward pitch of surface 590 and proximal upward pitch of surface 591 serve to substantially retain boss 542 in upward distal terminus 538 until the practitioner applies sufficient direct downward force to digital activation section 534 to downwardly deflect first cantilever 532.

Figure 37:
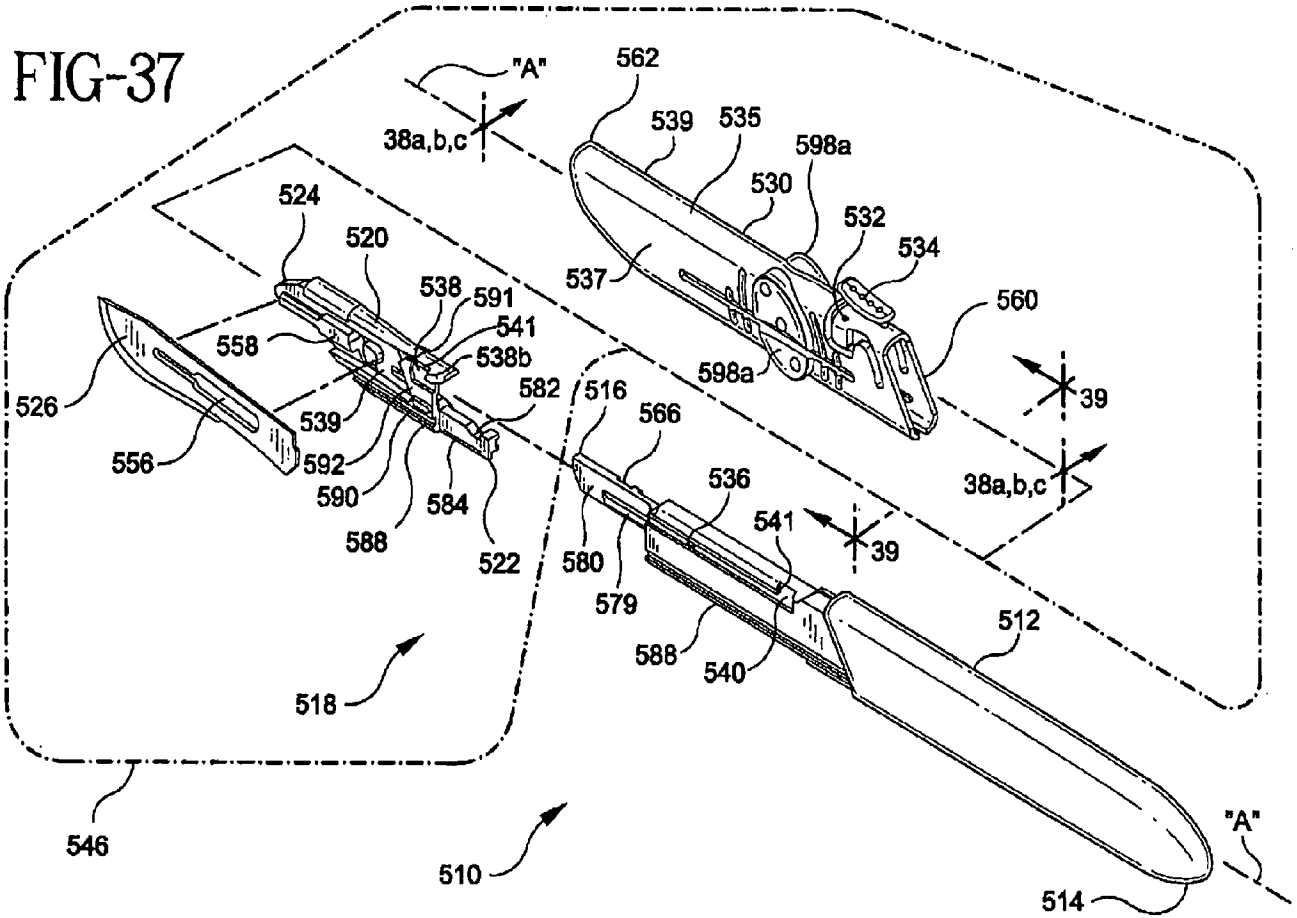
FIG. 37 is a perspective view of another preferred embodiment of the scalpel of the invention.
Figure 38A:
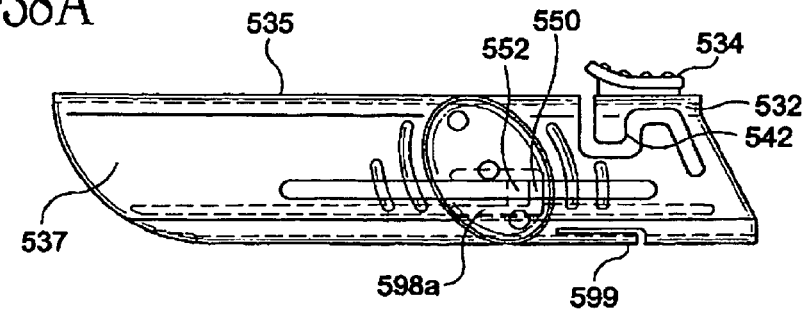
FIG. 38a is a side elevational view of the shield portion of the scalpel of FIG. 37 taken along the line 38a,b,c-39a,b,c.
Figure 39:
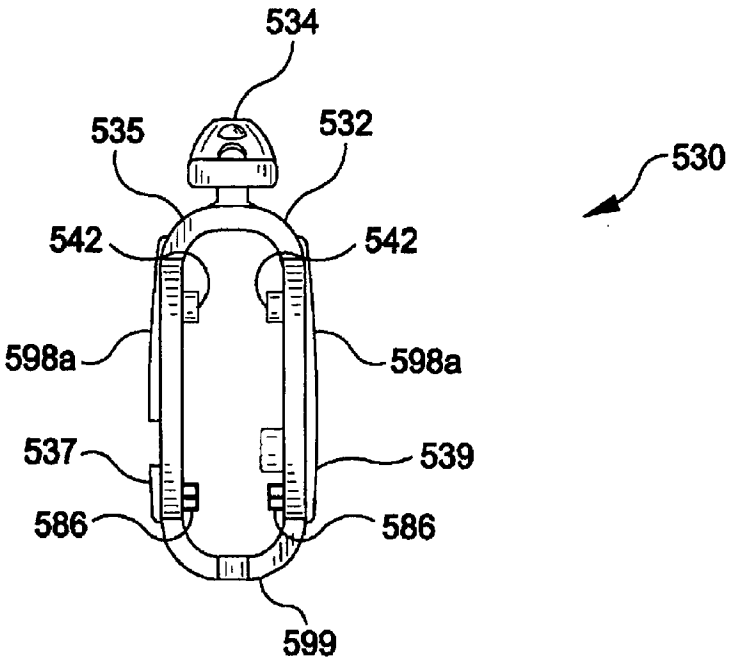
FIG. 39 is a view of the shield of FIG. 37 taken along the line 39-39.
Figure 40B:
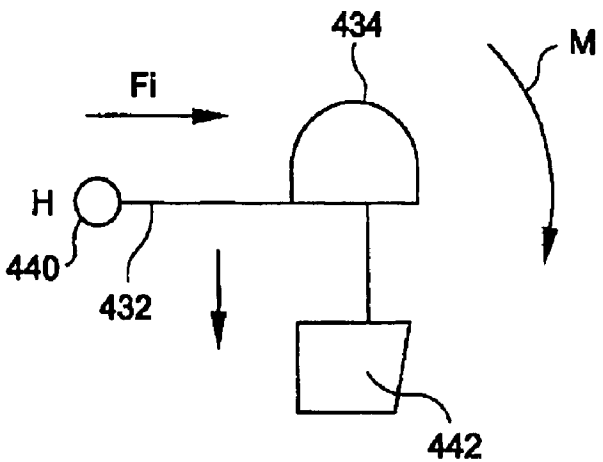
Figure 40A:
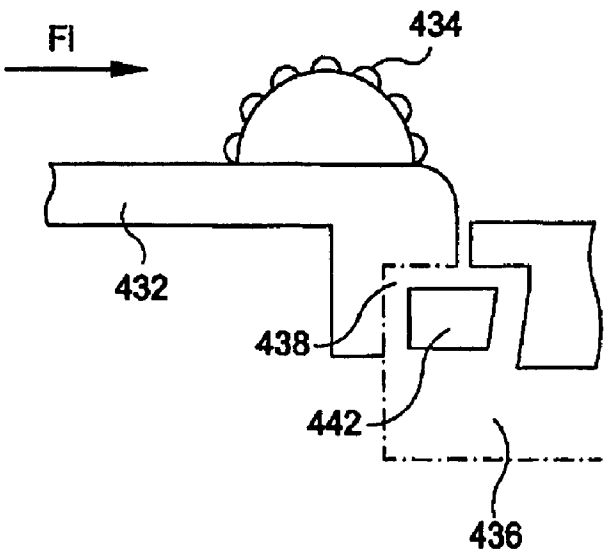
FIG. 40a is a schematic view of the cantilever portion of the shield of the embodiment shown in FIGS. 25-36c.
Figure 40D:
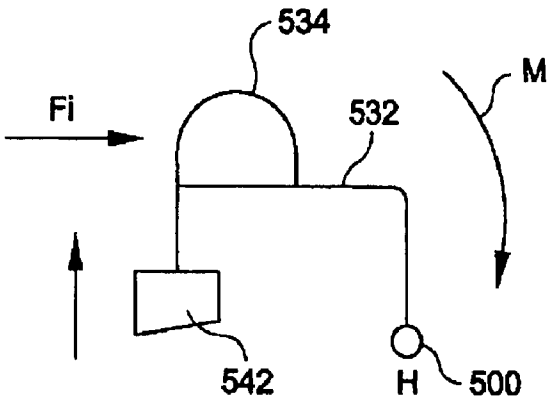
FIG. 40d is a diagram of the cantilever portion of the shield of the embodiment shown in FIGS. 37-39.
Figure 40C:
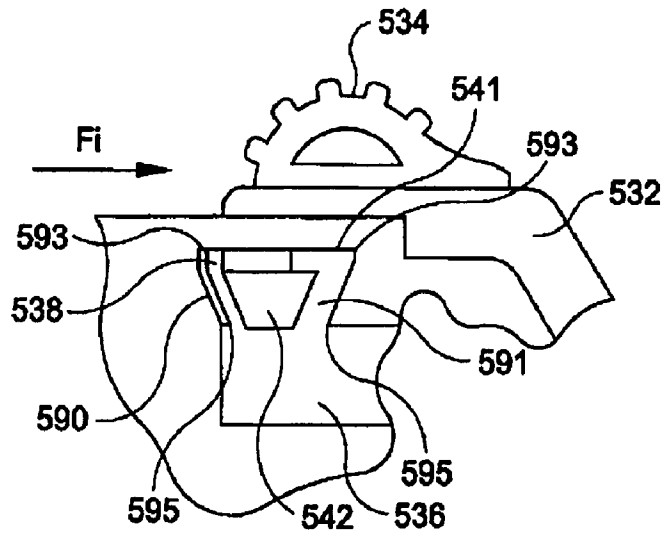
FIG. 40c is a schematic view of the cantilever portion of the shield of the embodiment shown in FIGS. 37-39.

In this embodiment, preferred first cantilever 532 extends distally from proximal end 560 of shield 530. Referring to FIGS. 40a and 40b, which is are schematic representations of a portion of shield 430 of the embodiment shown in FIGS. 25-36c, and FIGS. 40c and d, that are schematic representations of a portion of shield 530 as illustrated in FIGS. 37-39, the reason for the preferred configuration of cantilever 532 is seen. In the embodiment of shield 430 with cantilever 432, if a practitioner inadvertently applies proximal force $F_i$ to the [distal] *digital* application section 434 during the mounting of cartridge 418 onto handle 412, resultant moment M is seen in FIG. 40b with a concomitant resultant to move boss 432 downwardly from distal termina 438 thereby potentially, if the force is sufficient, inadvertently releasing shield 430 for proximal movement to expose blade 426. Referring now to FIGS. 40c and 40d, illustrating the preferred configuration of cantilever 532, it is apparent that the application of the same proximal force $F_i$ to digital application section 534 results in a concomitant resultant to move boss 532 upwardly in distal termina 538. Diagrams comparing these resultants are seen in FIGS. 40b and 40d. The upward resultant on boss 532 and the downward resultant on boss 432 are shown in FIGS. 40d and 40b respectively. The placement of the effective hinges $H_{400}$ and $H_{500}$ of the cantilevers 432 and 532 provide the direction of the resultant action on the bosses 432 and 532. When the preferred cantilever 532 configuration is coupled with the distal upward pitch of surface 590 and proximal upward pitch of surface 591 in distal upward termina 538 in the preferred scalpel 510, the probability of an inadvertent release of shield 530 for proximal movement during mounting of cartridge 518 onto handle 512 is substantially reduced.

Referring again to FIGS. 37-39c, additional ergonomic features to direct the practitioner's finger placement during mounting of the cartridge to the handle are shown. A finger placement surface 598a is preferably present on each of a first side 537 and a second side 539 of shield 530, with several other preferred configurations illustrated as 598b and 598c in FIGS. 38a, 38b, and 38c. In preference testing, configuration 598c is most preferred and includes a preferably roughened surface finish difference from preferably transparent sides 537 and 539 to provide a visual direction and to facilitate the practitioner's grip during mounting and dismounting of cartridge 518 to handle 512.

Figure 38B:
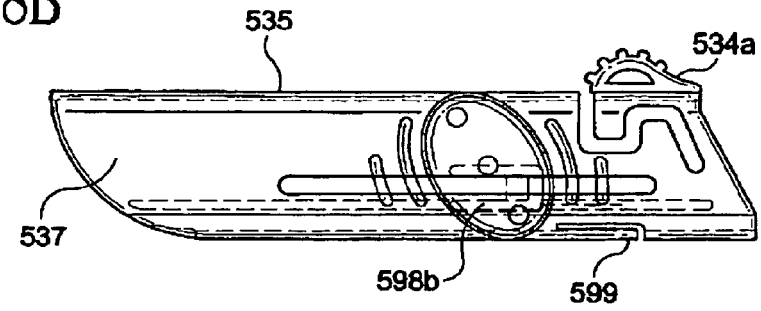
FIG. 38b is a side elevational view of an alternate embodiment of the shield portion, analogous to FIG. 38a, of the scalpel of FIG. 37.
Figure 38C:
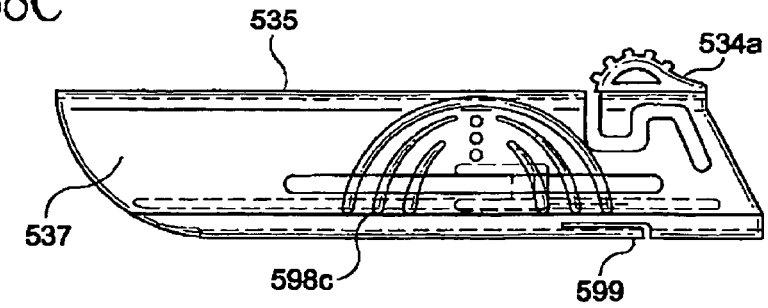
FIG. 38c is a side elevational view of yet another alternate embodiment of the shield portion, analogous to FIG. 38a, of the scalpel of FIG. 37.

In FIGS. 38b and 38c, a more preferred configuration for digital activation section 534a is illustrated. This more preferred configuration reduces any inadvertent force applied by the practitioner to cantilever 532 during mounting cartridge 518 to handle 512, while facilitating the [intention] *intentional* movement of shield 530 to the proximal position to expose blade 526 for its intended use.

A further element to substantially further reduce the possibility of inadvertent proximal movement of shield 530 during mounting of cartridge is best seen in FIGS. 38a, 38b and 38c. A second cantilever 599 is disposed on the bottom of shield 530. Second cantilever 599 is disposed with a fixed distal end and a free proximal end so that if a practitioner grasps cartridge 518, in a not recommended manner, at the top and the bottom for mounting cartridge 518 onto handle 512, second cantilever 599 will be deflected upwardly so that the free end engages blade holder 520 and substantially prevents proximal movement of shield 530.

Cartridge 518 is preferably supplied sealed in a package 546 illustrated in phantom in FIG. 37 as formed from materials substantially resistant to the passage of microorganisms and exposed to conditions that render any microorganisms within the package substantially non-viable. Suitable materials for forming the package include, but are not limited to, paper, polymeric films, non-wovens, metallic foils, and combinations of these materials. Suitable conditions for rendering microorganisms non-viable include, but are not limited to, chemical agents such as ethylene oxide and gaseous hydrogen peroxide, ionizing radiation such as gamma, electron beam, ultra-violet and the like.

Cartridge 518 is supplied separately and includes blade holder 520 and blade 526 in package 546. Blade 526 is preferably formed from a material such as stainless steel, carbon steel or a ceramic that is suitable for being formed to a sharpened edge for cutting. Shield 530 is substantially not movable with respect to blade holder 520 unless cartridge 518 is properly fully mounted on handle 512 and the practitioner handling the scalpel is intentionally moving the shield. Practitioners and service personnel are thus substantially protected from inadvertent exposure to the blade during assembly of the cartridge to the handle, during handling to prepare for or after a procedure, or during clean-up and disposal of a cartridge after removal from the handle. Shield 530 preferably includes a deflectable tab 550, seen in phantom in FIGS. 38 a, b and c, with an inwardly projecting lug 552 that is disposed to engage a seat 554 in blade holder 520. During initial assembly of cartridge 518, preferred blade 526 with an aperture 556 is fixedly attached to an outward protuberance 558 on blade holder 520 by fitting aperture 556 over protuberance 558 so that blade 526 is substantially rigid with respect to blade holder 520. Suitable fixed attachments of blade 526 to blade holder 520 are formed by heat staking the projection onto the aperture, adhesive bonding or the like. Shield 530 has a proximal end 560 and a distal end 562. The assembly then includes substantially axially aligning proximal end 560 of the shield with distal end 524 of the blade holder and proximally advancing the shield onto the blade holder to form cartridge as shown in FIG. 37. Tab 550 with inwardly projecting lug 552 is disposed to engage seat 554 in blade holder 520 when bosses 542 are in distal termina 538, thus substantially preventing further movement of shield 530 with respect to blade holder 520 until cartridge 518 is mounted onto handle 512.

Preferably, shield 530 is substantially prevented from movement with respect to blade holder 520 during mounting of cartridge 518 onto handle 512 even if the practitioner unintentionally applies sufficient pressure to digital activation surface 545 to deflect cantilever 532. Proximal end 514 of handle 512 is preferably disposed to engage at least one of bosses 542 as cartridge 518 is proximally advanced onto handle 512 when cantilever 532 is deflected downwardly. Additionally if the practitioner were to inadvertently apply pressure to digit activation surface 534 after cartridge 518 is partially properly advanced onto handle 512, preferred handle 512 further includes a recess 566 disposed on a top surface 567 of handle 512 to engage at least one of bosses 542 to function as a false stop and substantially prevent further advancement of cartridge 518 onto handle 512.

As cartridge 518 is fully seated on handle 512, a distal prong 578 on handle 512 with a chamfered surface 570 is preferably disposed to engage tab 550 and disengage inwardly projecting lug 552 from seat 454 on blade holder 520, thus allowing movement of shield 530 with respect to blade holder 520 when the practitioner intentionally applies sufficient pressure to digital activation surface 534 to downwardly deflect cantilever 532. Preferably, distal prong 578 is stiffened by a rib 579 on one side.

Cartridge 518 is releasably mounted to handle 512 by engaging a downward projection 580 on handle 512 with a pocket 582 on a flexible beam portion 584 that projects proximally from blade holder 520. To remove cartridge 518 from handle 512, cartridge 518 is distally advanced from handle 512. Preferably, shield 530 substantially surrounds blade holder 520 and substantially prevents inadvertent access to blade 526 when shield 530 is in the distal position. When shield 530 is proximal, blade 526 is exposed for use, bosses 542 are disposed in proximal termina 540 and shield 530 surrounds at least a portion of handle 512. Since shield 530 substantially surrounds at least a portion of the handle when *it* is in the proximal *p* position, beam 584 is substantially prevented from flexing downwardly to release projection 580 from pocket 582 by the shield, thus substantially preventing cartridge 418 from being dismounted from handle 512 when the blade is exposed. Additionally, if a practitioner inadvertently applies distal force to attempt to move the shield to the distal position, the presence of bosses 542 in proximal termina 540 substantially prevent movement of shield 530 to the distal position. To move shield 530 to the distal position, the practitioner must apply sufficient force to the digital activation surface 534 to downwardly deflect cantilever 532 and release bosses 542 from the proximal termina 540. If a practitioner grasps shield 530 and attempts to remove cartridge 418 from handle 412 after shield 430 is released from the proximal position, but before shield 530 is fully seated in the distal position and blade 526 is substantially protected from inadvertent access, shield 530 substantially prevents the disengagement of pocket 582 from projection 580 until the shield is distally advanced to substantially protect blade 526 from inadvertent access. Then, as handle 512 is separated from cartridge 518, prong 578 is disengaged from tab 550 thereby allowing lug 552 to engage seat 554 and substantially prevent movement of shield 530 with respect to blade holder 520.

Preferably, shield 530 includes inwardly projecting rails 586 disposed to slidably engage conjugate slots 588 on both sides of blade holder 520 and handle 512 to provide stability to shield 530 during movement between the proximal and distal positions and to improve the overall rigidity and feel of scalpel 510 in the practitioner's hand.

Blade holder 520 may be formed from materials such as polymeric resins or metallic materials. Preferably, blade holder 520 is formed from thermoplastic materials such as polypropylene, polyethylene, polycarbonate, polysulfone, polyacetal, polyamide and the like. Shield 530 may be formed from thermoplastic materials such as polypropylene, polyethylene, polycarbonate, polyacetal, polyamide and the like. For particular applications, the material selected to form shield 530 may be substantially transparent. Handle 512 may be formed from thermoplastic materials such as polyethylene, polycarbonate, polysulfone, polypropylene, polyacetal, polyamide and the like. Preferably, handle 512 is formed from a metallic material such as formed powdered metal or machined metal. Preferably materials are selected to provide a substantially rigid structure for scalpel 510 that are compatible with most sterilization methods and provide practitioners with a scalpel that has similar "feel" and "balance" to current reusable devices or reusable handle devices intended to mount and dismount bare single-use blades.

In normal use, practitioners would receive cartridge 518 sealed in package 546. A method for assembling scalpel 510 includes opening package 546 to expose cartridge 518, and positioning the cartridge so that proximal end 522 of the blade holder is in substantial axial alignment with the distal end of handle 512. The practitioner then advances the cartridge proximally onto the handle until it is fully seated. At this point, the practitioner may apply finger pressure to the digital activation surface to downwardly deflect the cantilever and release the shield for movement from the distal position to the proximal position to expose the blade for use. After the use of the blade is complete, the practitioner releases the shield from the proximal position with finger pressure and moves shield 530 to the distal position. The practitioner then grasps the shield, applies distal force and removes the cartridge from the handle for disposal according to the institution's disposal protocol.

What is claimed is:

1. A surgical scalpel comprising:

an elongate handle defining a longitudinal axis and having a proximal end and a distal end;

a cartridge removably mounted to said handle, said cartridge including a blade holder with a proximal end and a distal end;

a blade fixedly attached to said blade holder disposed so that said blade projects distally outwardly when said cartridge is mounted to said handle;

said cartridge including a shield having proximal end, a distal end and a bottom, said shield being mounted onto said blade holder and shield being slidably movable between a distal position wherein said shield substantially prevents inadvertent access to said blade and a proximal position wherein said shield substantially surrounds a portion of said handle and said blade is exposed for use, said cartridge including means for releasably mounting said cartridge to said handle and for substantially preventing said movement of said shield with respect to said blade holder unless said cartridge is mounted on said handle, said cartridge further including at least one means for substantially preventing an inadvertent movement of said shield to said proximal position thereby to expose said blade as said cartridge is being mounted to said handle.

2. The surgical scalpel of claim 1 wherein a first means for substantially preventing said inadvertent movement of said shield to said proximal position comprises a first cantilever on said shield extending [distally] from said proximal end of said shield, said first cantilever having a digital activation section projecting upwardly from a top surface of said shield.

3. The surgical scalpel of claim 2 wherein said first means for preventing said movement of said shield with respect to said blade holder further comprises said handle and said blade holder having at least one groove having a distal terminus on said blade holder and a proximal terminus on said handle, said groove extending proximally from said blade holder onto at least a distal portion of said handle, said at least one groove having an upward enlargement at said distal terminus and an upward enlargement at said proximal terminus.

4. The surgical scalpel of claim 3 wherein said first means for preventing said movement of said shield between said distal position and said proximal position further includes at least one inwardly projecting boss disposed on first cantilever to engage said at least one groove, said boss projecting into said distal terminus when said shield is in said distal position, said boss projecting into said proximal terminus when said shield is in said proximal position, said shield thereby being normally latched in one of said proximal and distal positions unless said first cantilever is downwardly deflected thereby disengaging said boss from said termina and allowing said slidable movement of said shield between said proximal position and said distal position.

5. The scalpel of claim 4 further including means for substantially preventing said cartridge from being mounted on said handle when said first cantilever is deflected downwardly, thereby substantially preventing inadvertent exposure of said blade during mounting said cartridge onto said handle.

6. The scalpel of claim 5 wherein said means for substantially preventing said cartridge from being mounted on said handle when said first cantilever is being deflected downwardly includes said distal end of said handle being disposed to engage said at least one boss on said cantilever when said first cantilever is downwardly deflected and said cartridge is being mounted to said handle thereby to substantially prevent said cartridge from being mounted on said handle.

7. The scalpel of claim 4 further including means for substantially preventing movement of said shield with respect to said blade holder during mounting said cartridge on said handle when said cartridge is partially properly mounted on said handle and said cantilever is downwardly deflected.

8. The scalpel of claim 7 wherein said means for substantially preventing movement of said shield when said cartridge is partially properly mounted and said cantilever is downwardly deflected includes a recess on said handle disposed distally to said groove to function as a false stop and engage said boss on said cantilever when said cantilever is deflected downwardly substantially to prevent proximal movement of said shield before said cartridge is fully mounted on said handle and thereby to prevent said cartridge from being fully mounted on said handle and prevent movement of said shield from said distal position to said proximal position until said downward deflection of said cantilever ceases.

9. The surgical scalpel of claim 3 wherein said distal upward terminus of said groove in said blade holder further includes a distal surface and a proximal surface each having an upwardmost edge and a lower edge, and wherein said distal upwardmost edge is more distal than said distal lower edge, thereby causing a distal upward pitch to said distal surface, and said proximal upward most edge is more proximal than said proximal lower edge, thereby causing a proximal upward pitch to said proximal surface, to substantially retain said boss in said upward distal terminus until the practitioner applies sufficient direct downward force to said digital activation section to downwardly deflect said first cantilever.

10. The surgical scalpel of claim 9 wherein said proximal terminus and said distal terminus of said groove each further include a roof portion sufficient to substantially prevent upward disengagement of said boss from said termina.

11. The surgical scalpel of claim 10 wherein said blade holder and said handle have one groove on one side and another groove on an opposite side thereof.

12. The surgical scalpel of claim 11 wherein said first cantilever has one boss disposed to engage said one groove on one side of said blade holder and said handle and another boss disposed to engage said second groove on said opposite side of said blade holder and said handle.

13. The surgical scalpel of claim 1 wherein a second means for substantially preventing said proximal movement of said shield as said cartridge is mounted onto said handle comprises a second cantilever on said bottom of said shield, said second cantilever having a distal fixed end and a free proximal end so that if the practitioner inadvertently applies a force to said bottom of said shield as said cartridge is mounted to said handle, said second cantilever is deflected upwardly to engage said blade bolder and substantially prevent inadvertent proximal movement of said shield to expose said blade.

14. The surgical scalpel of claim 1 wherein a third means for substantially preventing inadvertent proximal movement of said shield as said cartridge is mounted to said handle comprises a finger grip portion on at least one of an outside surface of said shield, said finger grip portion being shaped to facilitate the practitioner's grip for mounting the cartridge onto said handle, thereby substantially preventing the practitioner's inadvertent contact with said digital activation section sufficient to deflect said first cantilever.

15. The scalpel of claim 1 wherein said means for releasably mounting said cartridge on said handle includes a downward projection on said handle and a flexible beam projecting proximally from said blade holder, said beam having a pocket therein for releasably engaging said downward projection on said handle to retain releasably said cartridge on said handle.

16. The scalpel of claim 15 wherein said means for releasably mounting said cartridge on said handle further includes means for substantially preventing said cartridge from being dismounted from said handle unless said shield is in said distal position.

17. The scalpel of claim 16 wherein said means for substantially preventing said cartridge from being dismounted from said handle unless said shield is in said distal position comprises said shield being disposed to prevent substantially said proximally projecting beam on said blade holder from being downwardly deflected and thereby to disengage said downward projection on said handle from said pocket on said beam unless said shield is in said distal position, thereby substantially preventing said pocket in said beam from disengaging from said downward projection on said handle and to retain said cartridge on said handle.

18. The scalpel of claim 1 wherein said means to substantially prevent movement of said shield with respect to said blade holder unless said cartridge is mounted on said handle includes a deflectable tab on a side of said shield having an inwardly projecting lug thereon disposed to engage a seat in said blade holder when said shield is in said distal position and said cartridge is not mounted on said handle thereby substantially preventing movement of said shield with respect to said blade holder.

19. The scalpel of claim 18 wherein said means for substantially preventing movement of said shield with respect to said blade holder unless said cartridge is mounted on said handle further comprises a distal prong on said handle disposed to engage said tab on said shield when said cartridge is mounted on said handle thereby to disengage said lug from said seat on said blade holder and to permit movement of said shield with respect to said blade holder.

20. The scalpel of claim 19 wherein said distal prong on said handle disposed to engage said tab on said shield further comprises a distal end having a chamfered surface to facilitate said disengagement of said lug from said seat.

21. The surgical scalpel of claim 1 wherein said blade is fixedly attached to said outward projection of said blade holder by a bonding selected from the group consisting of heat staking, mechanical cold forming and adhesive bonding.

22. The surgical scalpel of claim 1 wherein said blade holder is formed from a thermoplastic material selected from the group consisting of polypropylene, polyethylene, polycarbonate, polysulfone, polyacetal and polyamide.

23. The surgical scalpel of claim 1 wherein said shield is formed from a thermoplastic material selected from the group consisting of polypropylene, polyethylene, polycarbonate, polyacetal, and polyamide.

24. The surgical scalpel of claim 1 wherein said shield is formed from a substantially transparent material.

25. The surgical scalpel of claim 1 wherein said handle is formed from a material selected from the group consisting of machined metal, formed powdered metal and thermoplastic materials.

26. A cartridge useful for releasably mounting on a handle to form a scalpel comprises:

a blade holder with a proximal end and a distal end;

a blade fixedly attached to said blade holder disposed so that said blade projects distally outwardly when said cartridge is mounted to a handle;

said cartridge including a shield slidably mounted onto said blade holder, said shield being slidably movable between a distal position wherein said shield substantially prevents inadvertent access to said blade and a proximal position wherein said shield substantially surrounds a portion of the handle and said blade is exposed for use, said cartridge further including means to substantially prevent said movement of said shield to said proximal position unless said cartridge is mounted on the handle, to prevent movement of said shield between said proximal position and said distal position, to substantially prevent a dismounting of said cartridge from the handle unless said shield is in said distal position, and means to substantially prevent inadvertent movement of said shield from said proximal position to said distal position as said cartridge is being mounted on said handle.

27. The cartridge of claim 26 being placed in a sealed package formed from materials substantially resistant to the passage of microorganisms and exposed to conditions that render any microorganisms inside said package substantially nonviable.

28. A method for assembling a surgical scalpel having a shielded blade comprises:

providing an elongate handle defining a longitudinal axis and having a proximal end and a distal end;

providing a cartridge including a blade holder with a proximal end and a distal end, said cartridge including a blade fixedly attached to said blade holder disposed so that said blade projects distally outwardly when said cartridge is mounted to said handle, said cartridge further including a shield slidably mounted onto said blade holder, said shield being slidably movable between a distal position wherein said shield substantially prevents inadvertent access to said blade and a proximal position wherein said shield substantially surrounds a portion of said handle and said blade is exposed for use, said cartridge further including means to substantially prevent said movement of said shield to said proximal position unless said cartridge is mounted on said handle, to prevent movement of said shield between said proximal position and said distal position and to prevent substantially a dismounting of said cartridge from the handle unless said shield is in said distal position;

gripping said cartridge at said finger grip portion;

positioning said cartridge so that said proximal end of said cartridge is in substantial axial alignment with said distal end of said handle;

advancing said cartridge proximally onto said distal end of said handle until said cartridge is fully seated thereby forming said scalpel.

29. The method of claim [23] *28* further comprising a method for removing said cartridge from said handle grasping said shield at said finger grip portion; and applying a distal substantially axial force to said shield sufficient to overcome a resistance to deflect a beam having a pocket on said blade holder and disengage a downward projection on said handle from said pocket on said beam, thereby removing said cartridge from said handle, said distal force serving to move said shield to said distal position in the event that the shield is not in the distal position and allowing said beam to deflect.

*30. A cartridge that may be mounted on a handle to form a scalpel, comprising:*

*a blade holder with a proximal end, a distal end and an external surface;*

*a blade attached to said blade holder; and*

*a shield slidably mounted about said blade holder so as to be disposed about the external surface of the blade holder wherein the shield is movable between a distal position shielding the blade and a proximal position exposing the blade for use; wherein the shield includes means to substantially prevent proximal movement of the shield with respect to the blade holder unless the cartridge is mounted to a handle.*

*31. The cartridge of claim 30 wherein the cartridge includes a means for releasably mounting said blade holder to a handle.*

*32. The cartridge of claim 31 wherein the proximal end of the blade holder defines a beam with a pocket formed therein for engagement with a handle.*

*33. The cartridge of claim 32 wherein the blade holder includes a medial portion defining a recess therein for engagement with a handle.*

*34. The cartridge of claim 30 further including a latch that positively holds the shield in the distal position.*

*35. The cartridge of claim 34 wherein the latch is a cantilever on the shield.*

*36. The cartridge of claim 34 wherein the blade holder includes a sidewall that defines at least one substantially longitudinally extending groove.*

*37. The cartridge of claim 36 wherein the groove includes a distal end with an upturned stop portion.*

*38. The cartridge of claim 35 wherein the blade holder includes a sidewall that defines at least one substantially longitudinally extending groove and the cantilever includes an inward projection disposed in the groove.*

*39. The cartridge of claim 30 further including a means to prevent dismounting the cartridge from a handle unless the shield is in the distal position.*

*40. The cartridge of claim 39 wherein the shield defines a proximal portion that substantially surrounds the proximal end of the blade holder.*

*41. The cartridge of claim 32 wherein the shield defines a proximal portion that substantially surrounds the beam when the shield is in the proximal position.*

*42. The cartridge of claim 30 wherein the shield includes at least one finger placement surface with a discrete surface configuration that facilitates gripping of the shield by a clinician.*

*43. A cartridge that may be releasably mounted on a handle to form a scalpel, comprising:*

*a blade holder with a proximal end and a distal end;*

*a blade attached to said blade holder;*

*a shield slidably mounted on said blade holder so as to be movable between a distal position substantially surrounding the blade and a proximal position exposing the blade for use; and*

*a latch that substantially prevents proximal movement of the shield with respect to the blade holder unless the cartridge is mounted to a handle.*

*44. The cartridge of claim 43 wherein the blade holder includes a seat and the shield includes a tab with an inwardly projecting lug disposed in the seat when the shield is in the distal position.*

*45. The cartridge of claim 43 wherein the shield includes at least one finger placement surface with a discrete surface configuration that facilitates gripping of the shield by a clinician.*

*46. A surgical scalpel, comprising:*

*a handle having a proximal hand gripping portion having a distal end, an intermediate shank having a proximal end and a distal end connected at its proximal end to the distal end of the proximal hand gripping portion wherein the intermediate shank defines a substantially longitudinally extending groove therein, and a tang extending from a distal end of the intermediate shank;*

*a cartridge releasably mounted on the handle to form a scalpel including a blade holder with a proximal end and a distal end and*

*a blade attached to said blade holder wherein the blade holder defines a substantially longitudinally extending groove therein aligned with the groove formed in the intermediate shank; and*

*a shield slidably mounted about the cartridge so as to be movable between a distal position shielding the blade and a proximal position exposing the blade for use and having a latch associated with the shield and having an inward projection disposed in the groove to releasably hold the shield in the distal position and the proximal position.*

*47. The surgical scalpel of claim 46 wherein the blade holder defines a beam with a pocket formed therein for engagement with the handle.*

*48. The surgical scalpel of claim 47 further including a projection extending downwardly from the intermediate shank for engagement with the pocket formed in the beam.*

*49. The surgical scalpel of claim 47 wherein the shield defines a proximal portion that substantially surrounds the beam when the shield is in the proximal position.*

*50. The surgical scalpel of claim 46 wherein the groove includes an upturned proximal end and an upturned distal end and the latch is cantilevered to be biased upwardly.*

*51. The surgical scalpel of claim 50 wherein the latch snaps into the upturned proximal end of the groove to indicate that the shield is locked in the proximal position and the latch snaps into the upturned distal end of the groove to indicate that the shield is locked in the distal position.*

*52. The surgical scalpel of claim 46 wherein the shield includes at least one finger placement surface with a discrete surface configuration that facilitates gripping of the shield by a clinician.*

*53. The surgical scalpel of claim 46 wherein the distal portion of the handle defines a top cut-away portion extending along the length of the groove to facilitate movement of the latch.*

*54. The surgical scalpel of claim 53 wherein the top cut-away portion is defined by two ramped end portions.*

*55. The surgical scalpel of claim 46 wherein the shield includes at least one inwardly projecting rail and the handle includes at least one slot formed in the external surface and extending substantially along the distal portion of the handle such that the inwardly projecting rail is disposed in the slot to facilitate movement of the shield between the distal position and the proximal position.*

*56. The surgical scalpel of claim 46 wherein the shield covers a proximal portion of the blade when the shield is in the proximal position exposing the blade for use.*

* * * * *